(12) United States Patent
Kwon et al.

(10) Patent No.: US 10,827,126 B2
(45) Date of Patent: Nov. 3, 2020

(54) ELECTRONIC DEVICE FOR PROVIDING PROPERTY INFORMATION OF EXTERNAL LIGHT SOURCE FOR INTEREST OBJECT

(71) Applicant: Samsung Electronics Co., Ltd., Gyeonggi-do (KR)

(72) Inventors: Soon Hwan Kwon, Gyeonggi-do (KR); Jung Keun Cho, Seoul (KR); Hyun Mi Kwak, Gyeonggi-do (KR); Joon Ki Kim, Gyeonggi-do (KR); Sol Kim, Gyeonggi-do (KR); Myeong Gi Jeong, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 47 days.

(21) Appl. No.: 16/014,656

(22) Filed: Jun. 21, 2018

(65) Prior Publication Data

US 2018/0376072 A1 Dec. 27, 2018

(30) Foreign Application Priority Data

Jun. 21, 2017 (KR) .......................... 10-2017-0078329

(51) Int. Cl.
*H04N 5/232* (2006.01)
*H04N 5/235* (2006.01)
(Continued)

(52) U.S. Cl.
CPC ....... *H04N 5/23293* (2013.01); *A45D 44/005* (2013.01); *A61B 5/0059* (2013.01);
(Continued)

(58) Field of Classification Search
CPC ............. H04N 5/2351; H04N 5/23293; H04N 5/23222; H04N 5/23219; G06K 9/00281; G06K 9/00228
See application file for complete search history.

(56) References Cited

U.S. PATENT DOCUMENTS 4,911,544 A 3/1990 Walsh
8,315,461 B2 * 11/2012 Free ...................... G06T 15/06
382/181

(Continued)

FOREIGN PATENT DOCUMENTS

CN 106845455 6/2017
EP 2 919 142 9/2015
(Continued)

OTHER PUBLICATIONS

International Search Report dated Aug. 30, 2018 issued in counterpart application No. PCT/KR2018/005834, 11 pages.
(Continued)

*Primary Examiner* — Ngoc Yen T Vu
(74) *Attorney, Agent, or Firm* — The Farrell Law Firm, P.C.

(57) ABSTRACT

An electronic device and method are provided guiding image capturing based on property information of an external light source. The electronic device includes a camera, a display, and a processor. The processor is configured to obtain an image using the camera; identify a face included in the image; determine a first brightness value for a first region of the identified face and a second brightness value for a second region of the identified face; determine property information of an external light source for the identified face, based on the first brightness value and the second brightness value; and provide, through the display, guide information corresponding to the property information of the external light source for the identified face.

18 Claims, 15 Drawing Sheets

(51) Int. Cl.

| | | |
|---|---|---|
| G16H 40/63 | (2018.01) | |
| G16H 30/20 | (2018.01) | |
| A45D 44/00 | (2006.01) | |
| A61B 5/00 | (2006.01) | |
| G02B 27/02 | (2006.01) | |
| G06K 9/00 | (2006.01) | |
| G09G 3/34 | (2006.01) | |

(52) U.S. Cl.
CPC ............ *A61B 5/445* (2013.01); *G02B 27/024* (2013.01); *G06K 9/00281* (2013.01); *G09G 3/3406* (2013.01); *G16H 30/20* (2018.01); *G16H 40/63* (2018.01); *H04N 5/2351* (2013.01); *H04N 5/23222* (2013.01)

(56) References Cited

U.S. PATENT DOCUMENTS

| | | | | |
|---|---|---|---|---|
| 9,185,287 | B2 | 11/2015 | Sento | |
| 9,491,370 | B2* | 11/2016 | Yeo ....................... | H04N 5/2351 |
| 9,507,420 | B2* | 11/2016 | Tartz .................. | H04N 5/23293 |
| 9,906,719 | B2 | 2/2018 | Sento | |
| 10,075,653 | B2 | 9/2018 | Jeong et al. | |
| 2011/0074782 | A1* | 3/2011 | Hirotani ............. | G06K 9/00228 |
| | | | | 345/426 |
| 2011/0317031 | A1* | 12/2011 | Honda ............... | H04N 5/23219 |
| | | | | 348/229.1 |
| 2013/0033566 | A1 | 2/2013 | Sento | |
| 2014/0300779 | A1 | 10/2014 | Yeo et al. | |
| 2015/0261996 | A1 | 9/2015 | Kim | |
| 2016/0006941 | A1 | 1/2016 | Klm | |
| 2016/0028953 | A1 | 1/2016 | Sento | |
| 2016/0054903 | A1 | 2/2016 | Jeong et al. | |
| 2016/0125228 | A1* | 5/2016 | Son ........................ | A61B 5/442 |
| | | | | 382/118 |
| 2016/0205320 | A1 | 7/2016 | Sento | |
| 2016/0364602 | A1* | 12/2016 | Kim .......................... | G06T 7/73 |
| 2017/0236298 | A1* | 8/2017 | Vetter ................ | G06K 9/00362 |
| | | | | 348/77 |

FOREIGN PATENT DOCUMENTS

| | | |
|---|---|---|
| EP | 3 017 755 | 5/2016 |
| FR | 2 952 519 | 5/2011 |
| KR | 10-2016-0052309 | 5/2016 |
| KR | 1020170016248 | 2/2017 |

OTHER PUBLICATIONS

European Search Report dated Nov. 14, 2018 issued in counterpart application No. 18178718.5-1126, 8 pages.

* cited by examiner $$\text{Delta1} = \text{diff}(Y_L, Y_R)/\min(Y_L, Y_R) \quad \text{-------- 601}$$

$$\text{Delta2} = \text{diff}(Y_N, Y_P)/Y_P \quad \text{---------------- 603}$$

FIG. 6B

ELECTRONIC DEVICE FOR PROVIDING PROPERTY INFORMATION OF EXTERNAL LIGHT SOURCE FOR INTEREST OBJECT

CROSS-REFERENCE TO RELATED APPLICATION(S)

This application is based on and claims priority under 35 U.S.C. § 119 to Korean Patent Application No. 10-2017-0078329, filed on Jun. 21, 2017, in the Korean Intellectual Property Office, the disclosure of which is incorporated by reference herein its entirety.

BACKGROUND

1. Field

The present disclosure relates generally to providing property information of an external light source for an interest object.

2. Description of Related Art

As the interest in and the demand for skin care have increased, developments have been made on an application for measuring a skin state of a user's body, for notifying the user of a skin health state using the measured skin state information, and for recommending a skin care regimen or cosmetics based on the skin health state and an electronic device providing an execution environment of the application. For example, the electronic device may obtain an image of the user's skin using a camera, and may determine the skin state of the user by analyzing the image. Thereafter, the electronic device may output, on a display, an object corresponding to the determined skin health state of the user.

As part of the skin analysis, the electronic device may determine the presence of wrinkles, pigmentation, acne, etc., by using an imaging characteristic of the obtained image, e.g., a color difference from a surrounding skin region.

An electronic device for skin analysis may capture an image of the skin while an external light source is blocked by bringing the camera of the electronic device into close contact with the skin. In other words, the electronic device may control external factors that may influence the skin analysis, such as illuminance, a shadow, the color temperature of a skin, the alignment state of the skin region to be captured, shaking (or sharpness) in capturing, noise (or the sensitivity of an image sensor), etc.

However, an electronic device, such as a smartphone, may not be able to sufficiently control these external factors since a user often performs image capturing in an arbitrary environment. Accordingly, when the electronic device performs the skin analysis based on a captured image in which the external factors were not controlled, the accuracy in the skin analysis may be reduced. Consequently, results of the skin analysis may not fall within a specified error range, and thus, the reliability of the skin analysis is insufficient.

SUMMARY

Accordingly, the present disclosure is provided to address at least the above-mentioned problems and/or disadvantages and to provide at least the advantages described below.

An aspect of the present disclosure is to provide an electronic device supporting an image processing method that provides a guide to uniformly maintain at least a portion of external factors affecting skin analysis, when capturing an image for the skin analysis.

Another aspect of the present disclosure is to provide an electronic device supporting an image processing method, wherein an alignment state of a skin region is uniformly maintained, and thus, the consistency of a target to be analyzed is maintained when history information on a skin state is managed.

In accordance with an aspect of the present disclosure, an electronic device is provided, which includes a camera, a display, and a processor. The processor is configured to obtain an image using the camera; identify a face included in the image; determine a first brightness value for a first region of the identified face and a second brightness value for a second region of the identified face; determine property information of an external light source for the identified face, based on the first brightness value and the second brightness value; and provide, through the display, guide information corresponding to the property information of the external light source for the identified face.

In accordance with another aspect of the present disclosure, an electronic device is provided, which includes a camera, a display, and a processor. The processor is configured to obtain an image captured through the camera; determine a face in the image; determine a first region and a second region inside the determined face; calculate a first brightness value corresponding to the first region; calculate a second brightness value corresponding to the second region; determine a position of an external light source based on a difference value between the first brightness value and the second brightness value; and display, on the display, guide information corresponding to the determined position in association with the determined face.

In accordance with another aspect of the present disclosure, a computer-readable recording medium is provided, which has a program stored thereon for executing a method. The method includes obtaining an image through a camera; identifying a face included in the image; determining a first brightness value for a first region of the identified face and a second brightness value for a second region of the identified face; determining property information of an external light source for the identified face, based on the first brightness value and the second brightness value; and providing, through a display, guide information corresponding to the property information in association with the identified face.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 6B illustrates a method of comparing luminance values of comparative regions with each other, according to an embodiment;

DETAILED DESCRIPTION

Figure 1:
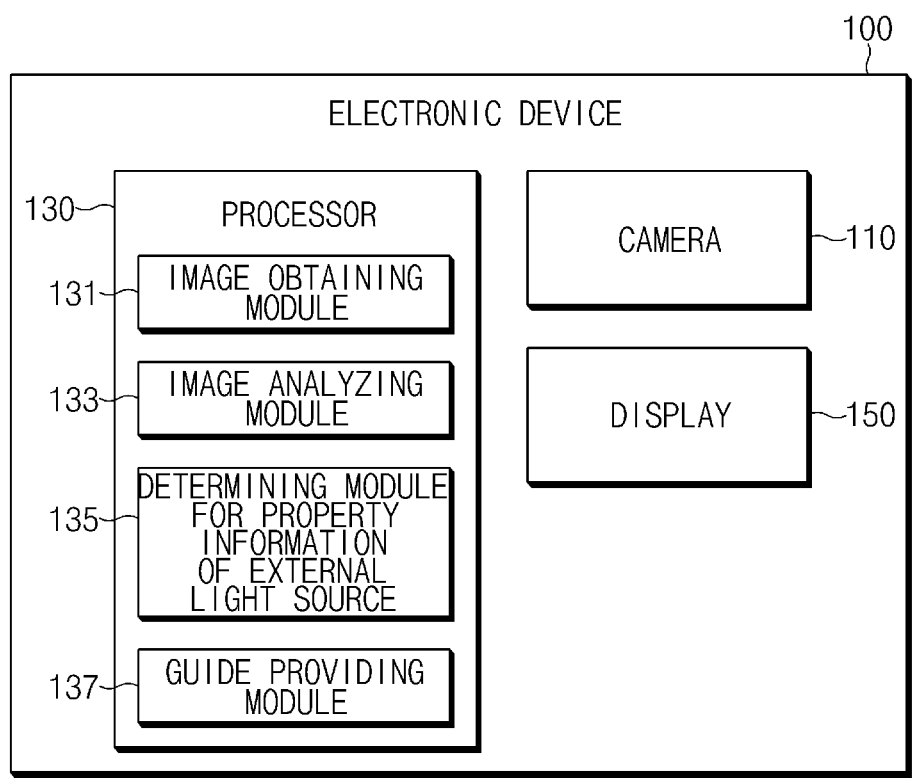
FIG. 1 illustrates an electronic device according to an embodiment.

Hereinafter, various embodiments of the present disclosure will be described with reference to accompanying drawings. However, those of ordinary skill in the art will understand that the present disclosure is not limited to a specific embodiment, and modifications, equivalents, and/or alternatives on the various embodiments described herein can be variously made without departing from the scope and spirit of the present disclosure.

Throughout the drawings and descriptions thereof, like reference numbers may be used to depict and reference the same or similar elements, features, and structures.

The various embodiments of the present disclosure and terms used herein are not intended to limit the technologies described in the present disclosure to specific embodiments, and it should be understood that the embodiments and the terms include modification, equivalent, and/or alternative on the corresponding embodiments described herein.

The terms of a singular form may include plural forms unless otherwise specified. The expressions "A or B", "at least one of A and/or B", "at least one of A and/or B", "A, B, or C", "at least one of A, B, and/or C", etc., as used herein may include any and all combinations of one or more of the associated listed items.

Numerical expressions such as "first," "second," etc., may be used to distinguish one element from another element, regardless of their priority or importance. When an element (e.g., a first element) is referred to as being "(operatively or communicatively) coupled with/to" or "connected to" another element (e.g., a second element), the first element may be directly coupled with/to or connected to the second element or an intervening element (e.g., a third element) may be present therebetween.

According to the situation, the expression "adapted to" or "configured to" used herein may be interchangeably used as "suitable for", "having the capacity to", "changed to", "made to", "capable of" or "designed to" in hardware or software. The expression "a device configured to" may indicate that the device is "capable of" operating together with another device or other components. For example, a "processor configured to (or set to) perform A, B, and C" may indicate a dedicated processor (e.g., an embedded processor) for performing corresponding operations or a generic-purpose processor (e.g., a central processing unit (CPU) or an application processor (AP)), which performs corresponding operations by executing one or more software programs which are stored in a memory device.

Herein, the term "module" may include a unit, which is implemented with hardware, software, or firmware, and may be interchangeably used with the terms "logic", "logical block", "component", "circuit", etc. A "module" may be a minimum unit of an integrated component or a part thereof or may be a minimum unit for performing one or more functions or a part thereof. A "module" may be implemented mechanically or electronically and may include, for example, an application-specific integrated circuit (ASIC) chip, a field-programmable gate array (FPGA), and a programmable-logic device for performing some operations, which are known or will be developed.

FIG. 1 illustrates an electronic device, according to an embodiment.

Referring to FIG. 1, an electronic device 100 includes a camera 110, a processor 130, and a display 150. However, the elements of the electronic device 100 are not limited thereto. For example, the electronic device 100 may include additional elements, such as a communication module (or a communication circuit) for communication with an external electronic device, a memory, etc.

The electronic device 100 may analyze a skin state of a part of a user body (e.g., the user's face) based on an image captured through the camera 110. For example, the electronic device 100 may determine the presence of wrinkles, pigmentation, or acne by using a feature of the captured image (e.g., a color difference between regions).

The electronic device 100 may provide a guide for controlling external factors, such as an illuminance, a shadow, a color temperature of the skin, the alignment of a skin region to be captured, a shake (or sharpness) in capturing, a noise, etc., which may influence the skin analysis using the image. For example, the electronic device 100 may display the position of an external light source on a preview image captured through the camera 110, and may guide a capturing composition (e.g., the position relationship between the camera 110 and the object) to minimize the influence of a shadow made by the external light source. As another example, the electronic device 100 may output, onto the preview image, an object guiding the alignment state (e.g., the size and the position of the face region) of a skin region to be captured. When the skin region to be captured (e.g., the face region) is aligned with the guide object by a user moving the camera 110 or the body of the user, the electronic device 100 may capture the skin region and may analyze the captured image. Accordingly, since the skin region to be subject to the skin analysis is consistent in the size and the position of the skin region, the history information of the skin state may be organically managed.

When the skin state of the user is determined by analyzing an image, the electronic device 100 including the communication module may transmit information on the skin state of the user to an external electronic device connected through the communication module. For example, the external device may be a server device associated with medical institutions, beauty companies, cosmetics companies, or shopping malls. In addition, the electronic device 100 may receive, from the external electronic device, feedback information based on the skin state of the user, e.g., recommendation information on skin treatment, a skin care regiment, cosmetics, skin-related goods, etc.

The electronic device 100 including the memory may store a command or data associated with at least one another element of the electronic device 100 in the memory. The memory may store a software and/or program. For example, the memory may store an application (e.g., a camera application) for supporting the image capturing through the camera 110. The memory may store an image captured through the camera 110. The memory may include a volatile memory and/or a non-volatile memory.

The memory may include a frame buffer that stores data corresponding to the captured image. For example, the frame buffer may store data corresponding to a preview image captured through the camera 110. The data may be transformed to be in a specified image format (e.g., a YCbCr format in which Y is a luminance component (or a brightness component), Cb and Cr are a color difference component, Cb represents the difference between the luminance and a blue component, and Cr represents the difference between the luminance and a red component) and the transformed result may be stored in the frame buffer. Preview images, which are sequentially captured, may be updated at a specified frame rate into the frame buffer.

The camera 110 may capture a still image or a moving image. The camera 110 may include at least one of a lens that receives image light of a subject and forms an image, an aperture that adjusts the amount of light passing through the lens, a shutter (or a shooting button) that opens and closes the aperture such that an image sensor is exposed to the light passing the lens for a specific time, the image sensor that receives, as an optical signal, the image formed through the lens, and an internal memory that may temporarily store the captured image. The internal memory may store the image formed through the image sensor before the shutter is manipulated.

The processor 130 may execute arithmetic operation or data processing associated with control and/or communication of the elements included in the electronic device 100. The processor 130 may control a plurality of hardware elements connected with the processor 130 by running an operating system (OS) or an embedded software program. The processor 130 may process a command or data received from at least one of other elements (e.g., a non-volatile memory) by loading the command or the data into the volatile memory and may store various pieces of data in the non-volatile memory. The processor 130 may process a command or data related to image processing, which is stored in the memory, in a specified program routine by loading the command or the data into the volatile memory. The processor 130 may include one or more CPUs, (APs), and communication processors (CPs).

The processor 130 may be electrically connected with the lens, the aperture, the image sensor, the shutter, and/or the internal memory, which is included in the camera 110, to control the function associated with the camera 110. The processor 130 may control a function such as auto focus, auto exposure, custom white balance, zoom in, zoom out, shooting, continuous shooting, timer shooting, flash on/off, filtering, etc., of the camera 110.

The processor 130 may include a plurality of modules to perform functions associated with image capturing, image analyzing or guide providing. The processor 130 includes an image obtaining module 131, an image analyzing module 133, a determining module 135 for property information of an external light source, and a guide providing module 137.

The image obtaining module 131 may obtain the image captured through the camera 110. The image obtaining module 131 may store the captured image in the internal memory included in the camera 110 or the memory. For example, the image obtaining module 131 may transform data corresponding to the captured image to be in a specified image format (e.g., the YCbCr format) and may store the transformed data in the frame buffer included in the memory. The image obtaining module 131 may store, in the internal memory, data corresponding to an image captured as the shutter is manipulated, and may store, in the memory, data corresponding to the captured image based on the occurrence of a specified user input from an input device and setting information.

The processor 130 may output an image captured through the camera 110 onto the display 150. For example, the processor 130 may output the image stored in the internal memory onto the display 150 as a preview image (or a live view image).

The image analyzing module 133 may analyze an image. The image analyzing module 133 may detect an object from the image. For example, the image analyzing module 133 may extract an edge of the object included in the image, based on image processing such as edge detection filtering. The image analyzing module 133 may detect, as one individual object, regions distinguished from each other by the edges.

The image analyzing module 133 may detect, as one individual object, the regions only when the shape of the edges corresponds to a predefined shape. The predefined shape may be an omega shape corresponding to the face shape of a human. The information associated with the predefined shape may be stored in the memory and managed.

The image analyzing module 133 may identify the detected object. The image analyzing module 133 may distinguish objects from each other by determining the property (e.g., the shape) for each object. The image analyzing module 133 may determine whether the object detected from the image is an object corresponding to a person, an animal, or an article. Further, the image analyzing module 133 may distinguish the objects from each other by determining the part (e.g., a face) of a human body, the type of the animal, or the type of the article.

The image analyzing module 133 may extract feature points from the object when the object included in the image is determined as an object corresponding to the face of the user. The feature point, which is a point representing the feature of a specific region to detect (e.g., the face part), trace, or recognize the specific region, may include an easily identifiable point from the image even if the shape, the size, or the position of each region of the image is changed. In addition, the feature point may include an easily identifiable point from the image even if the capturing angle of the camera 110 or the external light source (e.g., lighting) is changed. The feature point may be set to a corner point or a boundary point of each region. When the features point are extracted from the object, the processor 130 may detect a region corresponding to the part of the face, such as a cheek, a philtrum, or a bridge of the nose, based on the extracted feature points.

The image analyzing module 133 may set comparative regions in an object corresponding to a body part of the user (e.g., the user's face). The image analyzing module 133 may set, as comparative regions, a left region (e.g., a left cheek region or left cheekbone region) and a right region (e.g., a right cheek region or right cheekbone region), which are bilaterally symmetrical to each other, in the object corresponding to the face of the user. As another example, the image analyzing module 133 may set, as comparative regions, a region (e.g., the bridge of the nose) subject to the least influence of the shadow and a region (e.g., philtrum) subject to the greatest influence of the shadow in the object corresponding to the face of the user. The region subject to the least influence of the shadow may include a region that has the longest length protruding to the outside in the face region. The region subject to the greatest influence of the shadow may include a region that has the shortest length protruding to the outside (or has the longest length recessed inward) in the face region.

The image analyzing module 133 may calculate luminance values (or brightness values) for the set comparative regions. For example, the image analyzing module 133 may extract luminance components (e.g., Y values) of data corresponding to the comparative regions, respectively, from the data which is stored in the frame buffer after transformed to be in the specified image format (e.g., the YCbCr format).

The determining module 135 for property information of the external light source may determine the property information of the external light source by using the luminance values for the comparative regions. The property information of the external light source may include information on a position (e.g., the position relationship between the external light source and the subject) or a type of the external light source (e.g., the type of the external light may be classified based on the brightness of the external light source). The determining module 135 for property information of the external light source may compare the luminance values for the comparative regions with each other and may determine the position of the external light source by using the difference value between the luminance values, e.g., as will be described in more detail below with reference to FIGS. 5, 6A, and 6B.

When property information of the external light source is determined, the guide providing module 137 may create an object including the property information of the external light source and may output the created object onto the display 150. For example, the guide providing module 137 may create the object by using information on the position of the external light source and may output the created object onto the display 150. The object created by using the information on the position of the external light source may include information representing the position relationship between the subject captured through the camera 110 and the external light source.

The guide providing module 137 may output, onto the display 150, an object guiding a capturing composition (or a capturing direction) to minimize the influence of a shadow made by the external light source while outputting the object created by using the position information of the external light source. For example, the guide providing module 137 may output, onto the display 150, an object, which guides a user to turn his/her body left since a shadow may be made at a right side of the subject (e.g., the face of the user) when the external light source is positioned at the left side of front (e.g., a direction that the subject faces the camera 110) of the subject. Accordingly, when the user turns to the left such that the external light source is positioned at the front-central direction of the subject, light emitted from the external light source is uniformly irradiated to the front surface of the subject, minimizing the influence of the shadow.

The guide providing module 137 may output, onto the display 150, an object, which guides a user to turn his/her body to the right since a shadow may be made at a left side of the subject when the external light source is positioned at the right side of front of the subject. The guide providing module 137 may output, onto the display 150, an object, which guides a user to turn his/her body so that the external light source is directly behind the user since a shadow may be made at the whole region of the front of the subject when the external light source is positioned in the rear of the subject (in the case of backlight). Similarly, the guide providing module 137 may output, onto the display 150, an object guiding the movement of the user to directly face the external light source such that the light emitted from the external light source is uniformly irradiated to the front of the user.

The guide providing module 137 may output, onto the display 150, an object guiding an alignment state (e.g., the size and the position of the object corresponding to the face of the user) of the object, which is captured through the camera 110. For example, the guide providing module 137 may output, onto the display 150, an object (e.g., a fitting guide object) guiding the movement of the subject such that the subject is positioned at a specified region of the capturing region of the camera 110.

When the subject is positioned at the specified region of the imaging region of the camera 110, the processor 130 may perform a capturing function based on the input (e.g., an input of pressing the shutter) of the user or a setting value (e.g., a setting value for auto shooting). For example, the processor 130 may control the camera 110 to automatically capture the subject when the subject is matched (aligned) with the specified region.

When the subject is captured through the camera 110, the processor 130 may perform the skin analysis for the subject based on the captured image. For example, the processor 130 may determine the skin state of the subject based on colors that are expressed in the pixels of an image depending on the absorbance of light into the subject.

The display 150 may display various contents (e.g., a text, an image, a video, an icon, and/or a symbol) for a user. The display 150 may output an image captured through the camera 110. The captured image may include a preview image obtained before the shutter of the camera 110 is manipulated or a captured image obtained after the shutter is manipulated. The display 150 may include a liquid crystal display (LCD), a light-emitting diode (LED) display, an organic LED (OLED) display, a microelectromechanical systems (MEMS) display, and/or an electronic paper display. The display 150 may include a touch screen for receiving a touch, gesture, proximity, or a hovering input using an electronic pen or a part of a user's body.

As described above, an electronic device includes a camera, a display, and a processor. The processor may be configured to obtain an image for one or more external objects by using the camera, identify an interest object, which corresponds to a face, of the one or more external objects included in the image, wherein the identifying of the interest object includes determining, with respect to the interest object, a first region and a second region for recognizing the face, determine a first brightness value for the first region and a second brightness value for the second region, determine property information of an external light source for the interest object, at least based on the first brightness value and the second brightness value, and provide, through the display, guide information corresponding to the property information of the external light source for the interest object.

The processor may be further configured to obtain another image for the interest object when a difference value between the first brightness value and the second brightness value satisfies a specified condition.

The processor may be further configured to provide, through the display, a first indicator representing a reference for a size of the interest object and a second indicator varied depending on the size of the interest object, in association with the obtaining of the another image, before obtaining the another image.

The processor may be configured to obtain the another image, additionally based on determination that the first indicator is substantially equal to the second indicator in size.

The processor may be further configured to allow at least a portion of the guide information to include position information of the external light source.

The processor may be configured to allow the at least a portion of the guide information to further include information on guiding a capturing direction for positioning the external light source in a specified direction with respect to the interest object.

The electronic device may further include a memory, and the processor may be configured to transform data, which is corresponds to the image, to be in a specified image format and store, in the memory, the data, as at least a portion of the obtaining of the image.

The processor may be further configured to allowing at least a portion of the specified image format to include brightness information corresponding to the image.

The processor may be further configured to determine the first brightness value and the second brightness value, at least based on the brightness information.

The processor may be configured to obtain an image captured through the camera, determine an interest object corresponding to a face in the image, determine a first region and a second region inside the interest object, calculate a first brightness value corresponding to the first region and a second brightness value corresponding to the second region, determine a position of an external light source at least based on a difference value between the first brightness value and the second brightness value, and display, on the display, guide information corresponding to the position in association with the interest object.

The electronic device may further includes a memory, and the processor may be configured to transform data corresponding to the image to be in a specified image format and store, in the memory, the data, as at least a portion of the obtaining of the image.

The processor may be further configured to allow at least a portion of the specified image format to include brightness information corresponding to the image.

The processor may be configured to calculate the first brightness value and the second brightness value, at least based on the brightness information.

The processor may be configured to determine a specified region inside the interest object as the first region, and determine another specified region symmetrical to the specified region as the second region.

The processor may be configured to determine, as the first region, a region, which has the longest length protruding to an outside, inside the interest object, and determine, as the second region, a region, which has the shortest length protruding to the outside, inside the interest object.

The processor may be configured to allow at least a portion of the guide information to include information on guiding a capturing direction for positioning the external light source in a specified direction with respect to the interest object.

The processor may be further configured to display, on the display, another guide information associated with a state that the interest object is aligned with a specified region.

Figure 2:
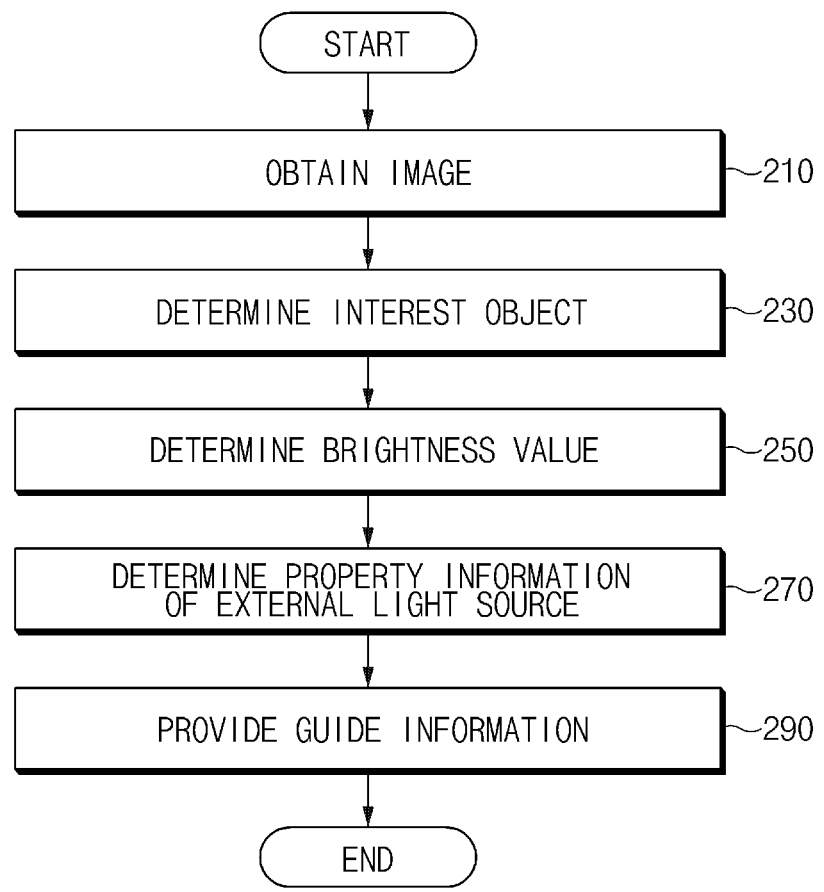
FIG. 2 is a flowchart illustrating a method of operating an electronic device, according to an embodiment.

FIG. 2 is a flowchart illustrating a method of operating an electronic device, according to an embodiment.

Referring to FIG. 2, in operation 210, a processor 130 of an electronic device 100 obtains an image for one or more external objects by using a camera 110. For example, the processor may obtain the image made by capturing a subject (e.g., the face of a user) by using the camera. The processor may obtain a preview image through the camera before a shutter is manipulated. The processor may transform data corresponding to the obtained image to be in a specified image format (e.g., the YCbCr format) and may store the transformed data in a frame buffer.

In operation 230, the processor determines an interest object, which corresponds to the face of the user, in the one or more external objects included in the image. For example, the processor may extract feature points from the obtained image. The processor may extract feature points from the image in order to detect the object included in the image and may detect, as one object (e.g., a face), a shape (e.g., an omega shape) made by adjacent feature points among the feature points. The feature point may be a corner point or a boundary point in the image. In addition, the processor may detect a face region.

The processor may detect the object included in the image by using the feature points and may determine whether the detected object corresponds to the face. The processor may determine whether the detected object corresponds to the face, by using information associated with predefined shapes stored in the memory. For example, the processor may determine whether the detected object corresponds to the face, by using information associated with the face shape (e.g., the omega shape) stored in the memory. When it is determined that the detected object corresponds to the face, the processor may detect (or determine), as a face region, a region occupied by the detected object in the image. The processor may determine the interest object corresponding to the face region by detecting (or determining) the face region.

The processor may determine, with respect to the interest object, a first region and a second region associated with recognizing the face, when determining the interest object. The first region and the second region may be used as comparative regions. The processor may set, as the comparative regions, a left region (e.g., a left cheek region or left cheekbone region) and a right region (e.g., a right cheek region or right cheekbone region), which are bilaterally symmetrical to each other, in the face region. For example, the processor may determine the left region as the first region and the right region as the second region.

The processor may set, as the comparative regions, a region (e.g., the bridge region of the nose) to be subject to the least influence of the shadow and a region (e.g., a philtrum region) to be subject to the greatest influence of the shadow in the face region. That is, the processor may determine, as the first region, a region, which has the longest length protruding to the outside, in the face region, and may determine, as the second region, a region, which has the shortest length protruding to the outside, in the face region. The comparative regions may be reference regions for determining the property information of the external light source.

In operation 250, the processor determines luminance values (brightness values) for the comparative regions. The processor may extract luminance components (e.g., Y values) of data corresponding to the comparative regions, respectively, from the data stored in the frame buffer after being transformed to be in the specified image format (e.g., the YCbCr format).

In operation 270, the processor determines the property information of the external light source by using the luminance values for the comparative regions. The processor may compare luminance values for the comparative regions with each other and may determine the position of the external light source by using the difference value between the luminance values. The processor may determine the type of the external light source or the number of external light sources by using the luminance values. For example, the processor may determine the types of the external light sources by classifying the external light sources depending on the brightness of the external light sources based on the sizes of the luminance values. As another example, the processor may determine shadow regions by using the luminance values and may determine the number of the external light sources based on the number of the shadow regions, the dark densities of the shadow regions, and/or the directions that the shadow region are inclined.

In operation 290, the processor provides guide information. The processor may create an object including property information of the external light source and may output the created object onto a display (e.g., the display 150). The processor may create an object by using position information of the external light source and may output the created object onto the display. The processor may output, on the display, an object, which guides a capturing composition (or a capturing direction), in order to minimize the influence of a shadow made by the external light source (to minimize the area of the shadow region). For example, the processor may determine a bias degree of the external light source based on the position information of the external light source and may output, on the display, an object providing a guide such that the external light source is positioned in a specified direction (e.g., the front central direction) with respect to the face.

Figure 3:
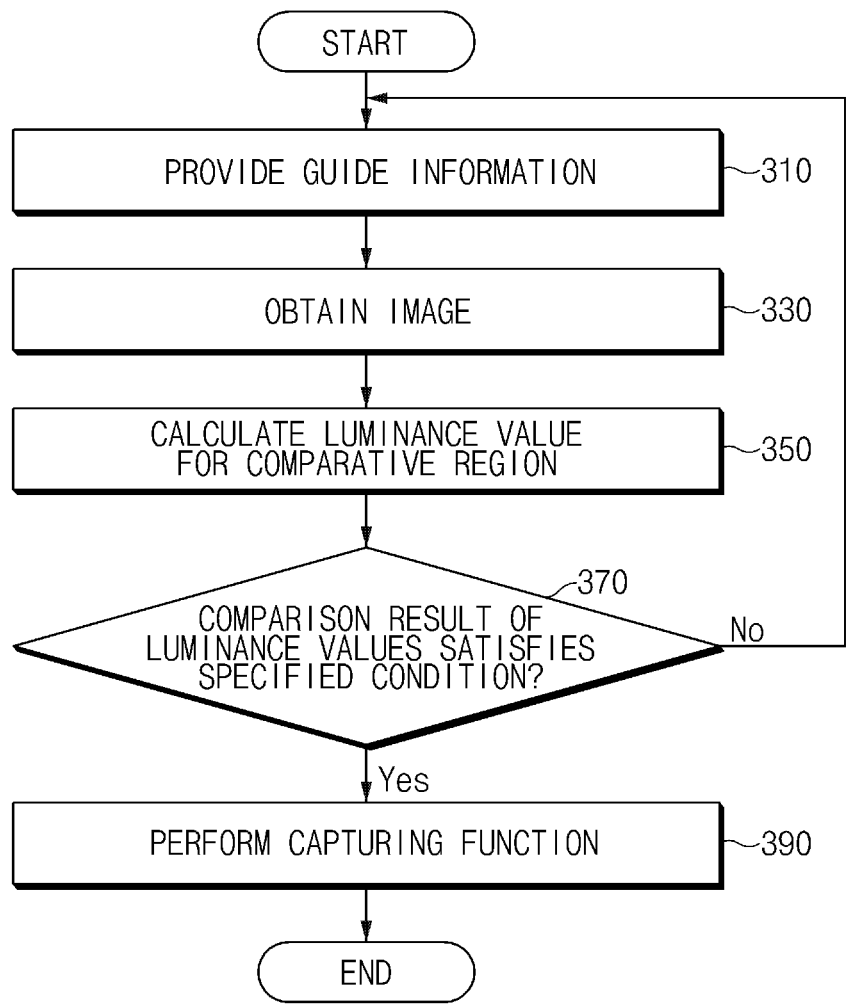
FIG. 3 is a flowchart illustrating a method of operating an electronic device, according to an embodiment.

FIG. 3 is a flowchart illustrating a method of operating an electronic device, according to an embodiment.

Referring to FIG. 3, in operation 310, a processor 130 of an electronic device 100 provides guide information. The processor may provide guide information identically or similarly to operation 290 of FIG. 2. The processor may create an object including property information of the external light source and may output the created object onto a display 150. The user may turn his/her face and/or a camera 110, based on the provided guide information, such that the external light source is positioned in a specified direction (e.g., a front central direction) with respect to the user's face.

In operation 330, the processor obtains an image by capturing a subject (e.g., the face of a user) through a camera 110. The processor may obtain the image identically or similarly to operation 210 of FIG. 2. The processor may obtain a preview image through the camera before a shutter is manipulated. The processor may transform data corresponding to the obtained image to be in a specified image format (e.g., the YCbCr format) and may store the transformed data in a frame buffer.

After having obtained the preview image, the processor may determine an interest object corresponding to the face of a user from the obtained preview image identically or similarly to operation 230 of FIG. 2. For example, the processor may extract feature points from the preview image and may detect an object included in the preview image by using the feature points. In addition, the processor may determine whether the detected object corresponds to a face.

When it is determined that the detected object corresponds to the face, the processor may determine, as a face region, a region occupied by the detected object in the preview image. In addition, the processor may set portions of the face region to comparative regions.

In operation 350, the processor determines luminance values for the comparative regions. The processor may determine the luminance values for the comparative regions identically or similarly to operation 250 of FIG. 2. For example, the processor may extract luminance components (e.g., Y values) of data corresponding to the comparative regions, respectively, from the data stored in the frame buffer after transformed to be in the specified image format (e.g., the YCbCr format).

In operation 370, the processor determines whether a comparison result of the luminance values satisfies a specified condition. The processor may determine whether the difference value between the luminance values is included in a specified size range. The specified size range may represent a range corresponding to a state that the external light source is positioned in a specified direction (e.g., the front-central direction) with respect to the face.

When the comparison result of the luminance values satisfies the specified condition in operation 370, the processor performs a capturing function in operation 390. For example, the processor may control the camera to capture a subject. The processor may output, onto the display, an object guiding an alignment state (e.g., the size and the position of the object corresponding to the face of the user) of the subject which is captured through the camera and may automatically perform the capturing function when the subject is positioned at a specified region of a imaging region of the camera. For example, the processor does not perform the capturing function when an object corresponding to a face is not positioned at the specified region of the imaging region of the camera even though the external light is positioned in the specified direction (e.g., the front-central direction) with respect to the face. When a user moves the face based on the provided guide information, and thus, the object corresponding to the user's face is positioned at the specified region of the imaging region of the camera, the processor may perform the capturing function.

When the comparison result of the luminance values does not satisfy the specified condition in step 370, the method returns to operation 310.

The processor may perform operations 310 to 370 until the comparison result of the luminance values for the comparison regions satisfies the specified condition. For example, the processor may provide an object including position information of an external light source and/or an object guiding a capturing composition until the external light source is positioned in the specified direction (e.g., the front central direction) with respect to the face.

Figure 4:
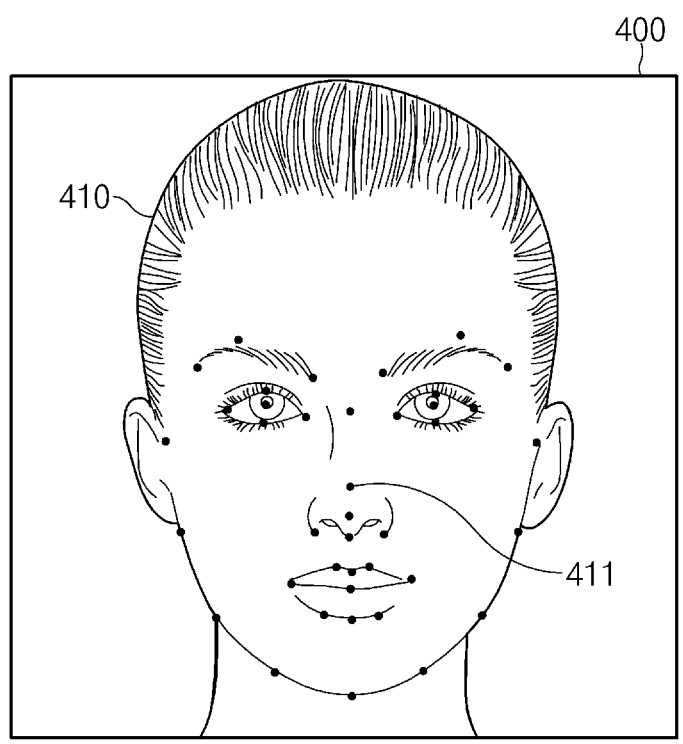
FIG. 4 illustrates a method of extracting feature points from an image, according to an embodiment.

FIG. 4 illustrates a method of extracting feature points from an image, according to an embodiment.

Referring to FIG. 4, a processor 130 of an electronic device 100 extracts a feature point 411 from an image 400 (e.g., a preview image) in order to detect an object (e.g., an object corresponding to a face) included in the image 400. The feature point 411 may include a corner point or a boundary point of a specific region in the image 400.

When adjacent feature points of the feature point 411, e.g., feature points positioned at a distance less than a specified size are connected with each other through a virtual line 410, and when the shape formed by the virtual line 410 corresponds to the shape of a face, the processor may determine a region inside the virtual line 410 as a facial region.

The processor may extract, as the feature points, a corner point or a boundary point of a region occupied by each facial part of the user. For example, the processor may extract, as the feature points, the corner point or the boundary point of the region occupied by an eyebrow, eye, nose, philtrum, lip, or chin part of the user.

Figure 5:
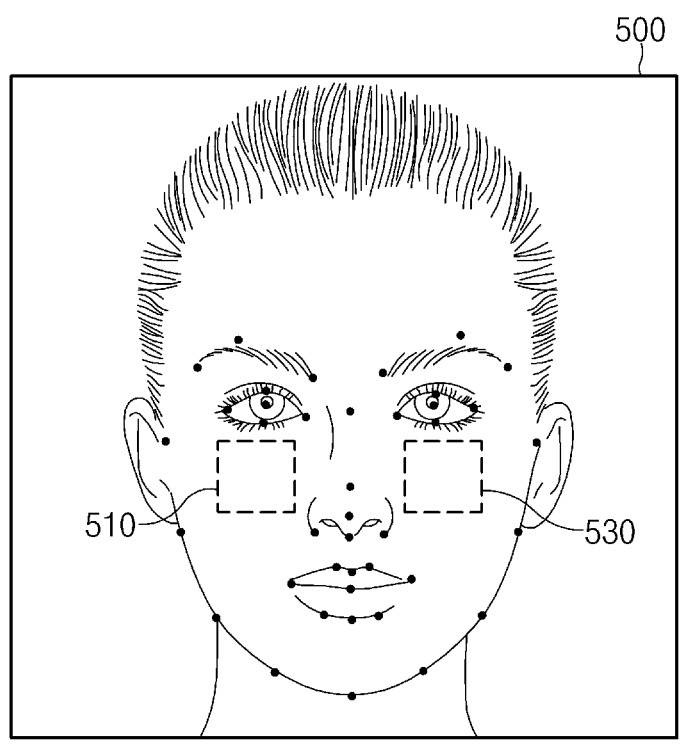
FIG. 5 illustrates a method of setting comparative regions in an image, according to an embodiment.

FIG. 5 illustrates a method of setting comparative regions in an image, according to an embodiment.

Referring to FIG. 5, when a shadow is made in a face region in capturing for skin analysis, a processor 130 of an electronic device 100 may not sufficiently analyze a region having the shadow in an image 500. More specifically, when the processor analyzes the image 500 by using an algorithm for analyzing skin, it may be difficult for the processor to determine the difference between a skin state of a face captured without a shadow and a skin state of a face captured with a shadow. Accordingly, the processor may provide guide information to capture an image of the face without a shadow in the face region.

For example, the forms of the shadow may include a side-surface shadow made when the external light source is biased to a left or right side from the front-center of the face and an up-down shadow made when the external light source is biased to an up or down side of a specific point (e.g., the end of a nose) of the face.

The processor may set, as comparative regions, left and right regions, which are bilaterally symmetrical to each other, in the face region such that the influence of the side-surface shadow is determined.

FIG. 5 illustrates the processor setting, as the comparative regions, a left cheekbone region 510 and a right cheekbone region 530. In this case, the processor may extract a first luminance component from data corresponding to the left cheekbone region 510 of the image 500 and may extract a second luminance component from data corresponding to the right cheekbone region 530 of the image 500. In addition, the processor may calculate the difference value between the first luminance component and the second luminance component. When the difference value is included in the specified size range, the processor may determine that the external light source is positioned at the front center of the face, that is, the influence of the side-surface shadow is minimized.

Figure 6A:
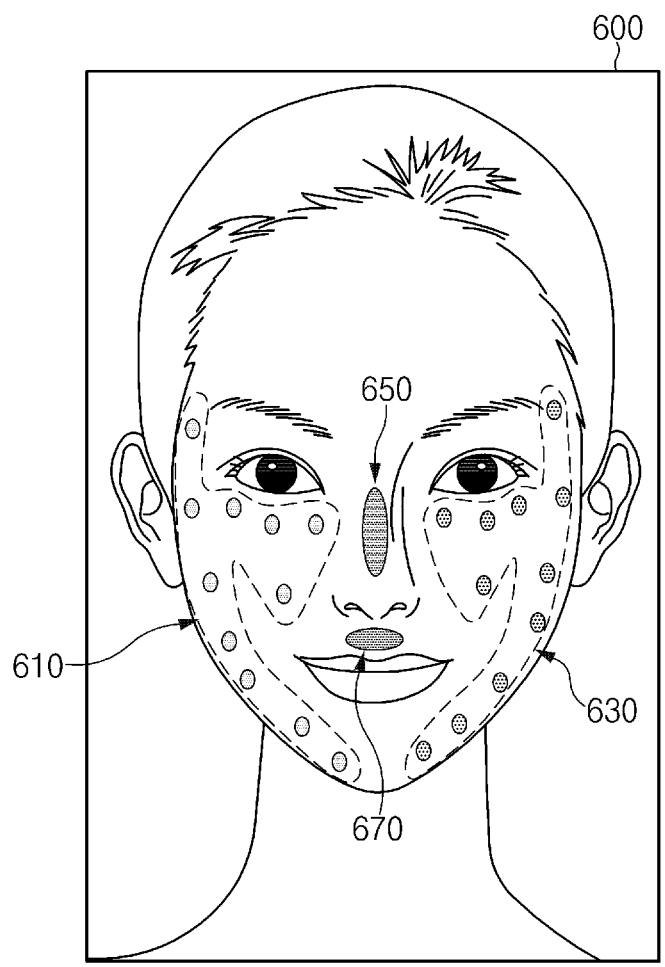
FIG. 6A illustrates a method of setting comparative regions in an image, according to an embodiment.

FIG. 6A illustrates a method of setting comparative regions in an image, according to an embodiment.

Referring to FIG. 6A, a processor 130 of an electronic device 100 may set, as comparative regions, regions, which are bilaterally symmetrical to each other (e.g., the left cheekbone region 510 and the right cheekbone region 530), in the face region so as to determine the influence of the side-surface shadow, as illustrated in FIG. 5. However, as illustrated in FIG. 6A, the processor may set, as comparative regions, a left region 610 (e.g., a region including a left cheek region and a left cheekbone region) and a right region 630 (e.g., a region including a right cheek region and a right cheekbone region), which are bilaterally symmetrical to each other, in the face region, a bridge region 650 of a nose that a shadow is rarely made, and a philtrum region 670 that a shadow is easily made so as to determine the influence of the side-surface shadow and the influence of the up-down shadow. However, the regions set as the comparative regions are not limited thereto. The processor may set, as to the comparative regions, specific regions on a virtual vertical line passing the bridge of the nose and the philtrum in the face region so as to determine the influence of the up-down shadow.

FIG. 6B illustrates a method of comparing luminance values of comparative regions with each other, according to an embodiment.

Referring to FIG. 6B, first Equation 601 and a second Equation 603 are used to compare luminance values for the comparative regions with each other. Specifically, the first Equation 601 is used to determine the influence of the side-surface shadow and the second Equation 603 is to determine the influence of the up-down shadow.

As illustrated in the first Equation 601, the processor calculates a difference value (diff (YL, YR)) between a first luminance component (YL) extracted from data corresponding to the left region 610 and a second luminance component (YR) extracted from data corresponding to the right region 630. Thereafter, the processor divides the calculated difference value by the minimum value (min (YL, YR)) between the first luminance component and the second luminance component and calculates a first comparison value (Delta1)

As illustrated in the second Equation 603, the processor calculates a difference value (diff (YN, YP)) between a third luminance component (YN) extracted from data corresponding to the bridge region 650 of the nose and a fourth luminance component (YP) extracted from data corresponding to the philtrum region 670. Thereafter, the processor divides the calculated difference value by the fourth luminance component and may calculate a second comparison value (Delta2). In the second Equation 603, the difference value is divided by the fourth luminance component because the fourth luminance component is generally less than the third luminance component.

Alternatively, the processor may calculate the first luminance component, the second luminance component, the third luminance component, and the fourth luminance component as average values of luminance values for the left region 610, the right region 630, the bridge region 650 of the nose, and the philtrum region 670, respectively.

The processor may also determine the influence of the shadow by the external light source as being minimized as the first comparison value and the second comparison value approximate specified values (e.g., a zero value).

Figure 7:
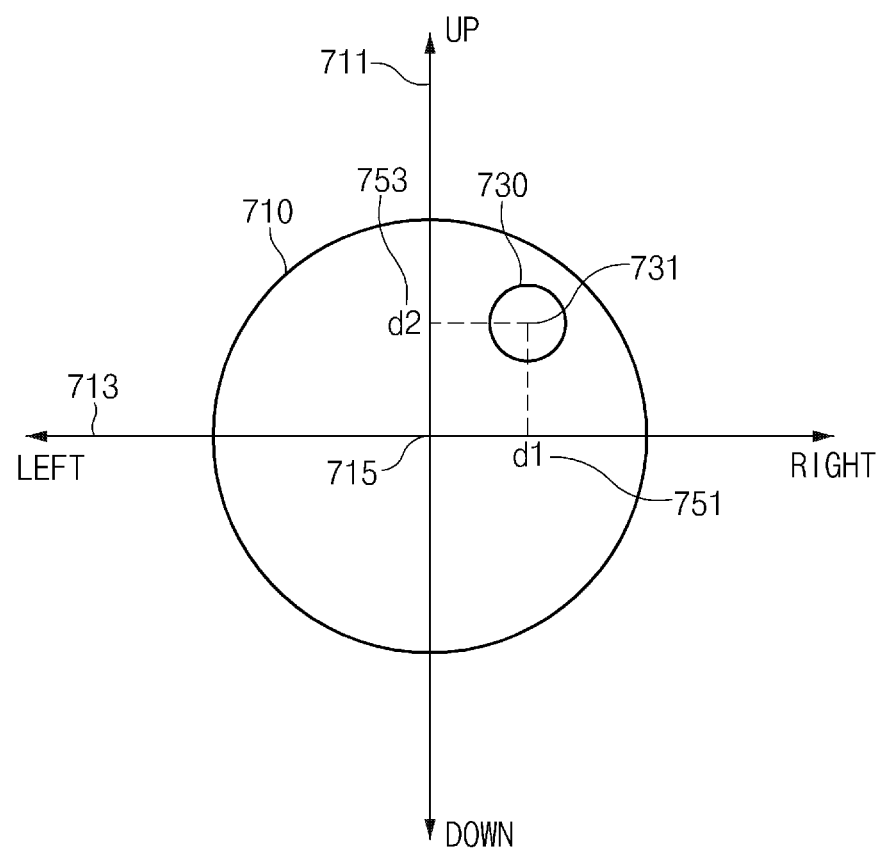
FIG. 7 illustrates an object guiding a position of an external light source, according to an embodiment.

FIG. 7 illustrates an object guiding a position of an external light source, according to an embodiment.

Referring to FIG. 7, a processor 130 of an electronic device 100 may create an object guiding the position of the external light source. The object may be created based on the comparison values (e.g., Delta1 or Delta2) of the luminance components calculated in FIG. 6B.

The object may include a vertical axis 711 and a horizontal axis 713. The vertical axis 711 may correspond to a virtual vertical line passing a bridge of a nose and a philtrum in a face region and the horizontal axis 713 may correspond to a virtual horizontal line passing an intermediate point of regions, which are bilaterally symmetrical to each other, in the face region. In addition, a first center point 715, at which the vertical axis 711 and the horizontal axis 713 meet each other, may correspond to a point at which the vertical line and the horizontal line meet each other.

The object may include a first circle 710 representing the range of sizes allowed for the comparison values. For example, the first center point 715 of the first circle 710 may correspond to a point at which the vertical axis 711 meets the horizontal axis 713.

The radius of the first circle 710 may correspond to the absolute value of the comparison value. Because the comparison value becomes a specific value in the range of '−1' to '+1', the radius of the first circle 710 may be '1'.

The object may include a second circle 730 representing the position information of the external light source. That is, the second center point 731 of the second circle 730 may correspond to the first comparison value (Delta1) and the second comparison value (Delta2) calculated through the first Equation 601 and the second Equation 603 of FIG. 6B, respectively.

For example, a horizontal-axis coordinate value (d1) 751 of the second center point 731 may correspond to the first comparison value representing the left-right bias degree of the external light source, and a vertical-axis coordinate value (d2) 753 of the second center point 731 may correspond to the second comparison value representing the up-down bias degree of the external light source. When the first comparison value is a negative (−) value, the horizontal-axis coordinate value (d1) 751 of the second center point 731 has a negative (−) value and is positioned at a distance moved leftward by an absolute value of the first comparison value from the first center point 715 on the horizontal axis 713. When the first comparison value is a positive (+) value, the horizontal-axis coordinate value (d1) 751 of the second center point 731 has a positive (+) value and is positioned at a distance moved rightward by an absolute value of the first comparison value from the first center point 715 on the horizontal axis 713.

As another example, when the second comparison value is a negative (−) value, the vertical-axis coordinate value 753 of the second center point 731 has a negative (−) value and is positioned at a distance moved downward by an absolute value of the second comparison value from the first center point 715 on the vertical axis 711. When the second comparison value is a positive (+) value, the vertical-axis coordinate value 753 of the second center point 731 has a positive (+) value and is positioned at a distance moved upward by an absolute value of the second comparison value from the first center point 715 on the vertical axis 711.

Figure 8:
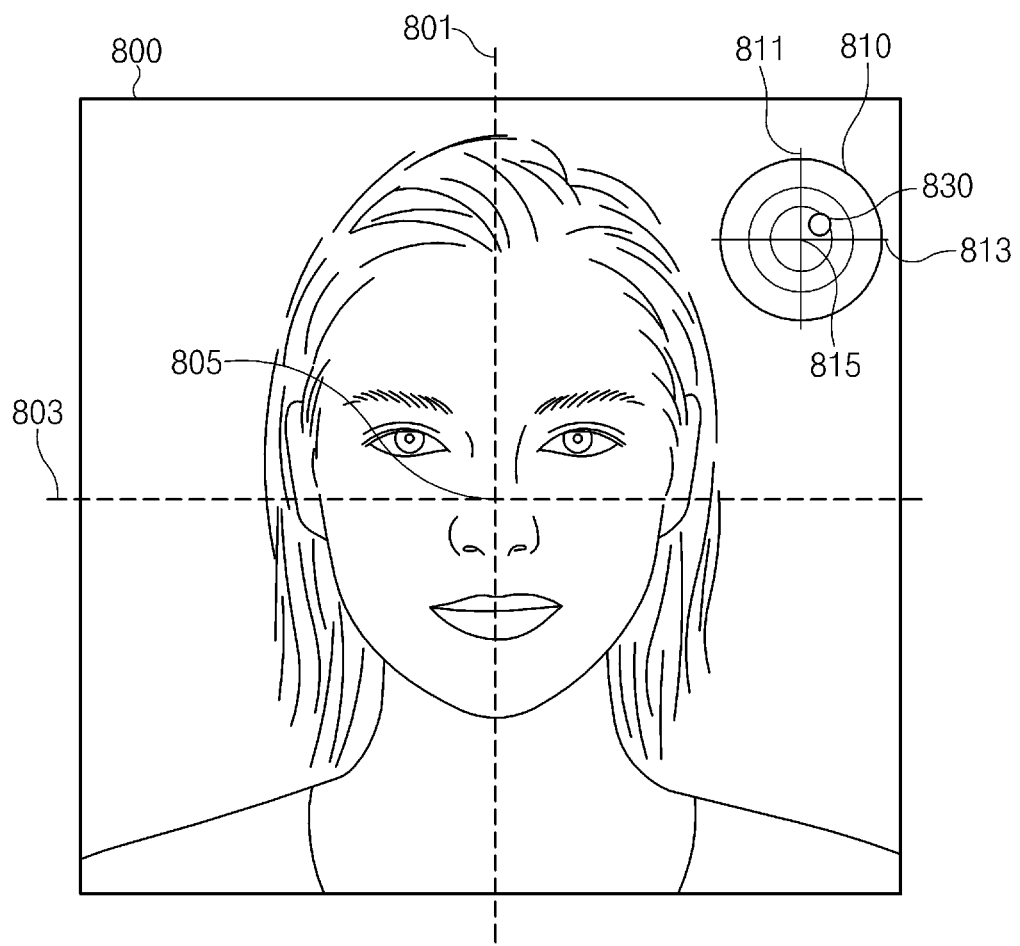
FIG. 8 illustrates a method of displaying an object guiding a position of an external light source on an image, according to an embodiment.

FIG. 8 illustrates a method of displaying an object guiding a position of an external light source on an image, according to an embodiment.

Referring to FIG. 8, a processor 130 of an electronic device 100 may display, on a display 150, an object guiding the position of the external light source. The processor may overlay the object with a specified region (e.g., a top-right region) of a preview image 800.

The processor may create an object in the form of a target board. For example, the processor may allow a vertical axis 811 of the object to correspond to a virtual vertical line 801 passing through the bridge of nose and a philtrum in a face region, and may allow a horizontal axis 813 of the object to correspond to a virtual horizontal line 803 passing the central part between regions, which are bilaterally symmetrical to each other, in the face region. In this case, a first center point 815, at which the vertical axis 811 and the horizontal axis 813 meet each other, may correspond to the intermediate point 805 at which the virtual vertical line 801 and the virtual horizontal line 803 meet each other.

In addition, the processor may further include, into the object, a first circle 810 representing the range of sizes allowed to the comparison values (e.g., Delta1 or Delta2) of the luminance components calculated in FIG. 6B, and also at least another circuit sharing the first center point 815 of the first circle 810 in the first circle 810. In addition, the processor may include, into the object, a second circle 830 representing position information of the external light source.

Figure 9:
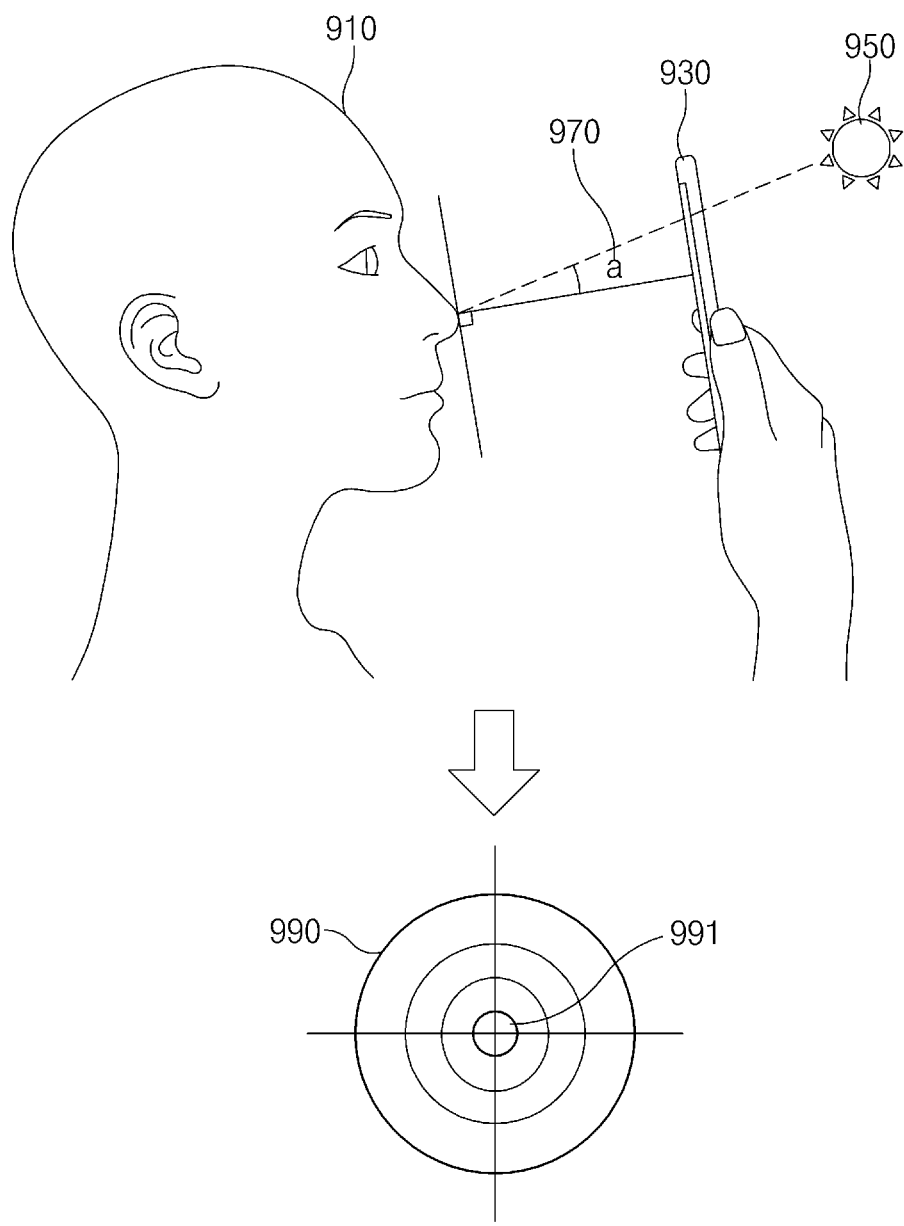
FIG. 9 illustrates a correlation between image quality and a position of an external light source, according to an embodiment.

FIG. 9 illustrates a correlation between image quality and a position of an external light source, according to an embodiment.

Referring to FIG. 9, a processor 130 of an electronic device 930 may guide a capturing composition such that image quality is improved by minimizing the influence of a shadow made by an external light source 950. In this case, the processor may create an object 990 guiding the capturing composition by using position correlation between the external light source 950 and a subject 910 (e.g., the face of a user).

The processor may determine, as the optimal capturing state, that the external light source 950 is positioned in a specified direction with respect to the subject 910. The specified direction may represent a direction of making, in specified size, an angle a 970 between a virtual line linking the subject 910 to a camera of the electronic device 930 and a virtual line linking the subject 910 to the external light source 950, such that the external light source 950 is positioned at the front (a direction facing the electronic device 930 from the subject 910) of the subject 910 without being biased left or right of the central vertical axis of the subject 910. When the external light source 950 is positioned in the specified direction, a circle (e.g., the second circles 730 and 830) representing position information of the external light source 950 may be marked on a center point 991 of the object 990.

Figure 10:
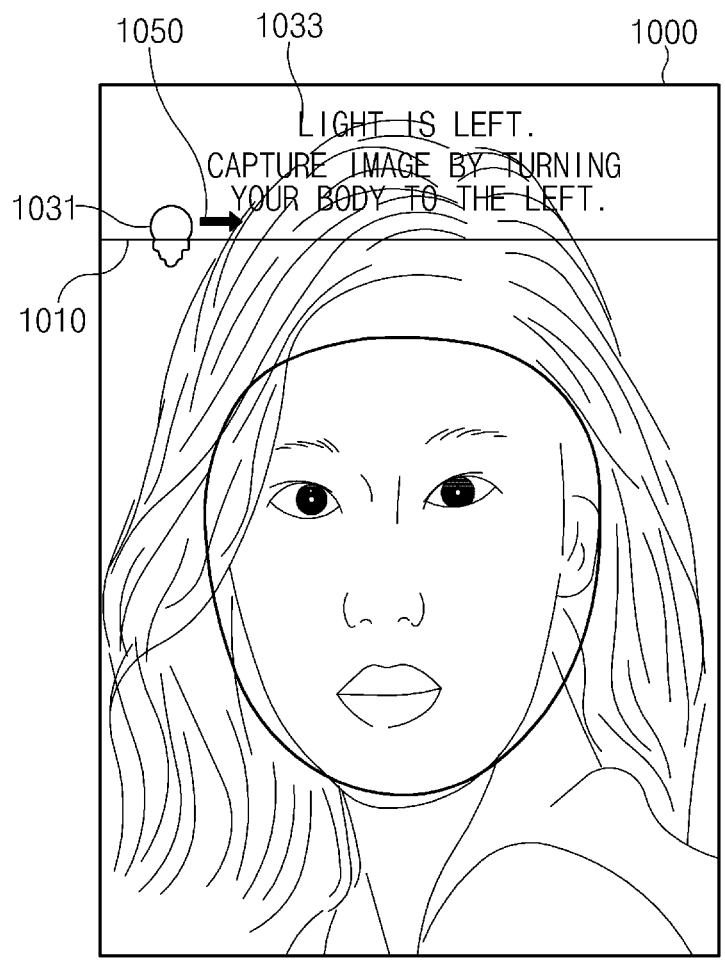
FIG. 10 illustrates a method of displaying an object guiding a position of an external light source on an image, according to an embodiment.

FIG. 10 illustrates a method of displaying an object guiding a position of an external light source on an image, according to an embodiment.

Referring to FIG. 10, a processor 130 of an electronic device 100 may determine a left-right bias degree of the external light source based on position information of the external light source and may display an object 1031 representing the left-right bias degree of the external light source on a horizontal axis 1010 of a preview image 1000. For example, when the external light source is biased leftward, the processor may display the object 1031 representing the left-right bias degree of the external light source at a left side of the horizontal axis 1010. When the external light source is biased right, the processor may display the object 1031 representing the left-right bias degree of the external light source at a right side of the horizontal axis 1010.

The processor may display the object 1031 representing the left-right bias degree of the external light source while further displaying an object 1033 providing a guide such that the left-right bias degree of the external light source is in a specified size range. Specifically, FIG. 10 illustrates the processor displaying the object 1033, in a text form, guiding a user to turn his/her body to the left, as the external light source is biased left.

When the user turns in one direction (e.g., left) based on the guide information included in the text object 1033, the processor may determine the left-right bias degree of the external light source again and may move the object 1031 representing the left-right bias degree of the external light source in a direction 1050 (e.g., right) opposite to the one direction (e.g., left) on the horizontal axis 1010.

Although only the left-right bias degree of the external light source has been described with reference to FIG. 10, the present disclosure is not limited thereto. According to various embodiments, the above description will be identically or similarly applied even to an up-down bias degree of the external light source.

Figure 11:
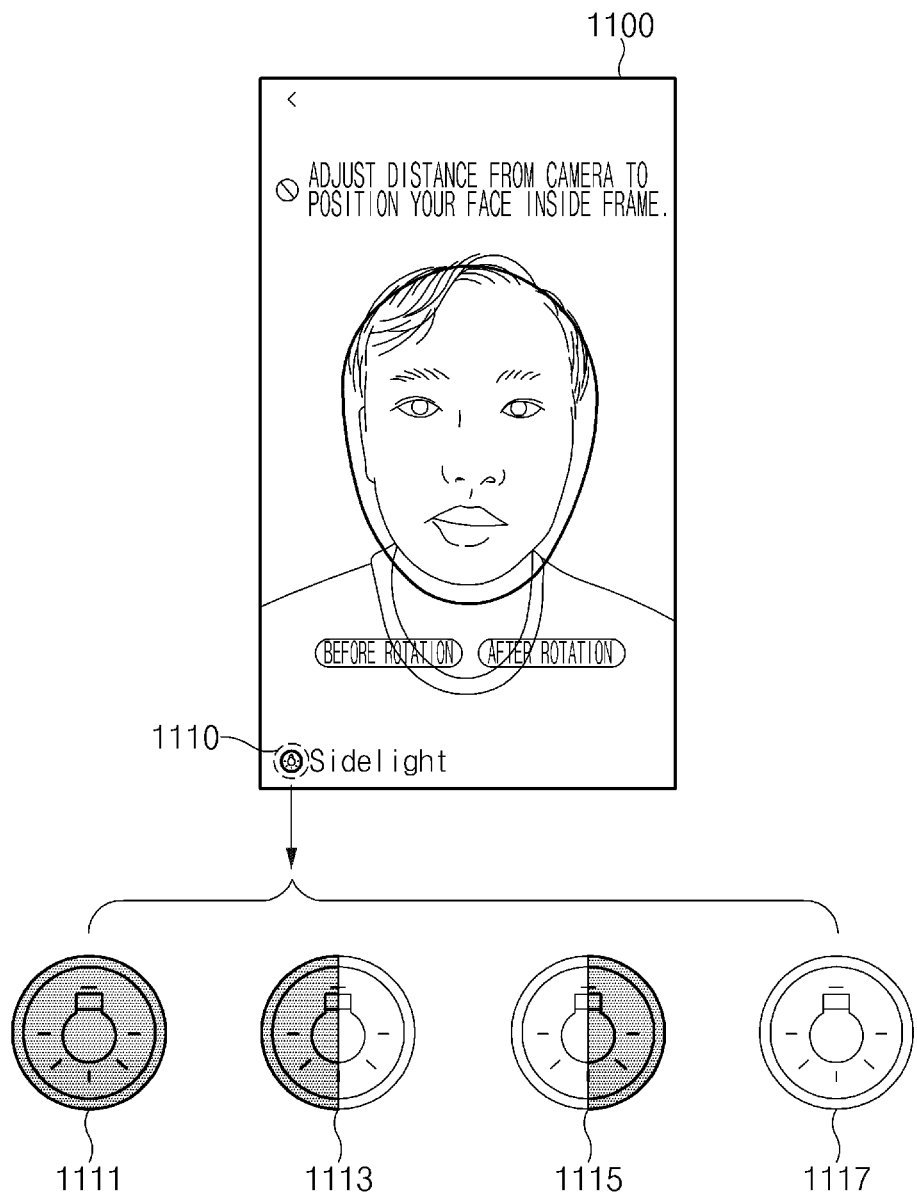
FIG. 11 illustrates a method of displaying an object guiding a position of an external light source on an image, according to an embodiment.

FIG. 11 illustrates a method of displaying an object guiding a position of an external light source on an image, according to an embodiment. Specifically, FIG. 11 illustrates a method of expressing a left-right bias degree of the external light source, which is determined based on position information of the external light source, by using a graphic characteristic.

Referring to FIG. 11, a processor 130 of an electronic device 100 may determine a left-right bias degree of the external light source based on position information of the external light source and may display an object 1110 representing the left-right bias degree of the external light source on a specified region (e.g., a bottom-left region) of a preview image 1100. The object 1110 representing the left-right bias degree of the external light source may include an image.

The processor may change an image corresponding to the object 1110 representing the left-right bias degree of the external light source, depending on the left-right bias degree of the external light source. For example, when the external light is positioned in the rear of a subject (e.g., backlight), the processor may change (specify) the image corresponding to the object 1110 representing the left-right bias degree of the external light source to a first image 1111. As another example, when the external light source is biased right, the processor may change (or specify) the image corresponding to the object 1110 representing the left-right bias degree of the external light source to a second image 1113. When the external light source is biased left, the processor may change (or specify) the image corresponding to the object 1110 representing the left-right bias degree of the external light source to a third image 1115. When the external light is not biased, the processor may change (specify) the image corresponding to the object 1110 representing the left-right bias degree of the external light source to a fourth image 1117.

The first image 1111 may have a totally dark background, and the fourth image 1117 may have a totally bright background. In addition, in the second image 1113, the right region of the background may be brighter than the left region of the background. In the third image 1115, the left region of the background may be brighter than the right region of the background.

Figure 12:
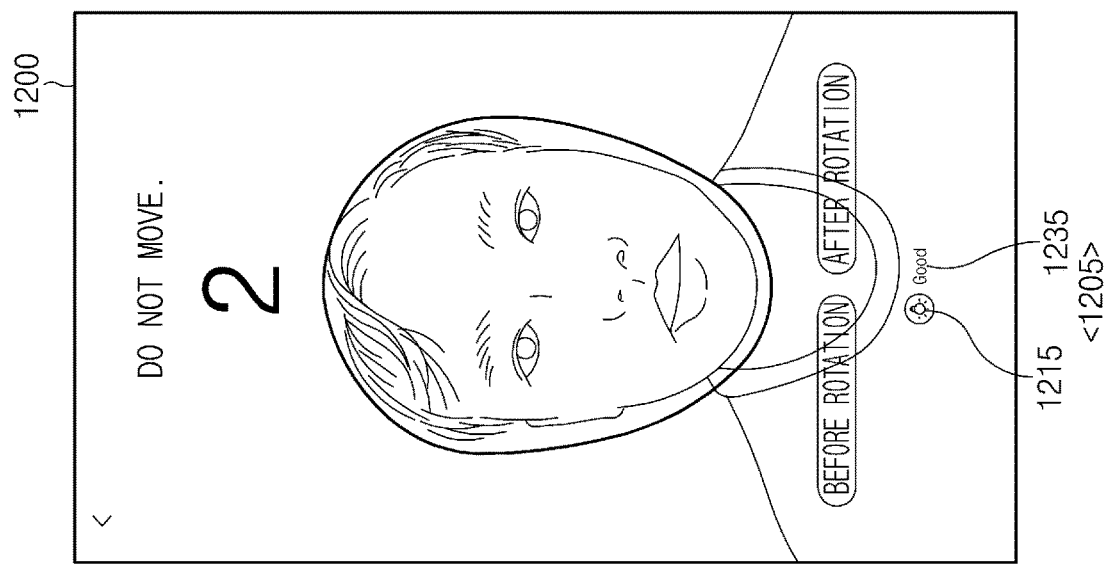
FIG. 12 illustrates a method of displaying an object guiding a position of an external light source on an image, according to an embodiment.
Figure 12:
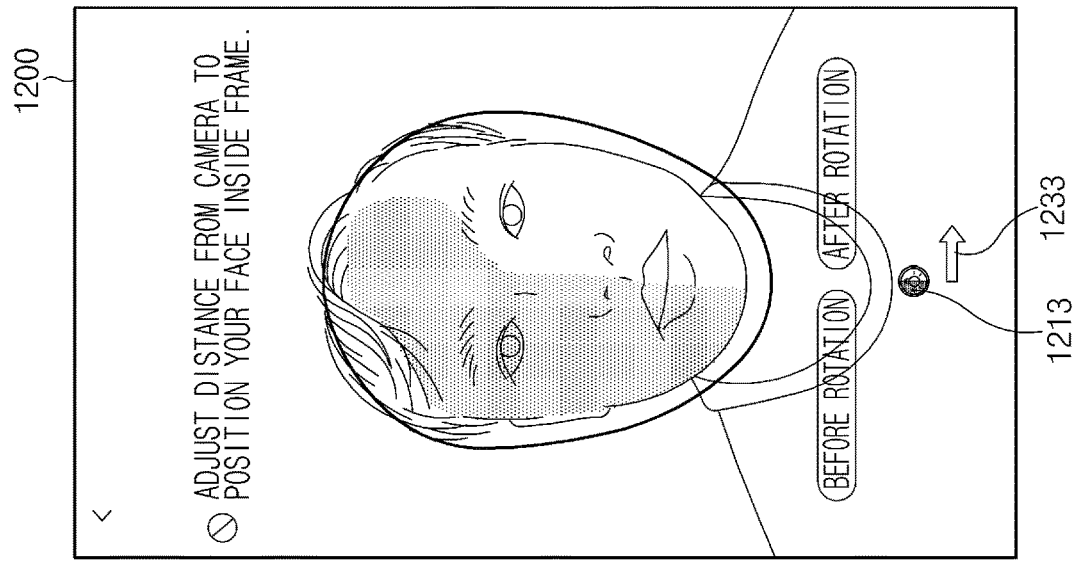
Figure 12:
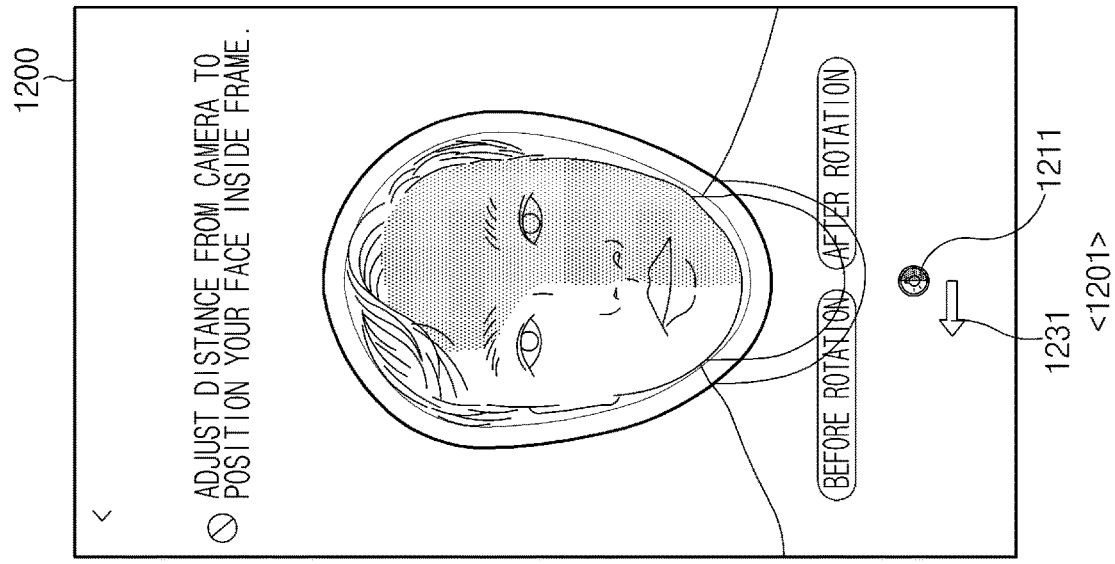

FIG. 12 illustrates a method of displaying an object guiding a position of an external light source on an image, according to an embodiment. Specifically, FIG. 12 illustrates a method of expressing a left-right bias degree of the external light source, which is determined based on position information of the external light source, by using a graphic characteristic and of additionally expressing an object providing a guide, such that the left-right bias degree of the external light source is included in a specified size range.

Referring to FIG. 12, a processor 130 of an electronic device 100 may determine a left-right bias degree of the external light source based on the position information of the external light source and may display an object representing the left-right bias degree of the external light source on a specified region (e.g., a bottom region) of a preview image 1200. The object representing the left-right bias degree of the external light source may include an image.

The processor may change an image corresponding to the object representing the left-right bias degree of the external light source, depending on the left-right bias degree of the external light source. For example, when the external light source is biased left, as illustrated in a first state 1201, the processor may change (or specify) an image corresponding to the object representing the left-right bias degree of the external light source to a first image 1211. However, when the external light source is biased right as illustrated in the second state 1203, the processor may change (or specify) the image corresponding to the object representing the left-right bias degree of the external light source to a second image 1213.

When the external light source is not biased as illustrated in a third state 1205, the processor may change (or specify) an image corresponding to the object representing the left-right bias degree of the external light source to a third image 1215.

In the first image 1211, the left region of the background may be brighter than the right region of the background. In the second image 1213, the right region of the background may be brighter than the left region of the background. In addition, the third image 1215 may have a bright background.

The processor may change the image corresponding to the object representing the left-right bias degree of the external light source depending on the left-right bias degree of the external light source while further displaying the object providing the guide such that the left-right bias degree of the external light source is included in the specified size range. For example, when the external light source is biased left as illustrated in the first state 1201, the processor displays a left arrow 1231 to guide a user to turn his/her body to the left. When the external light source is based right as illustrated in a second state 1203, the processor may display a right arrow 1233 to guide the user to turn his/her body to the right. The processor may display a text object 1235 representing a non-bias state when the external light source is not biased, as illustrated in the third state 1205.

Figure 13:
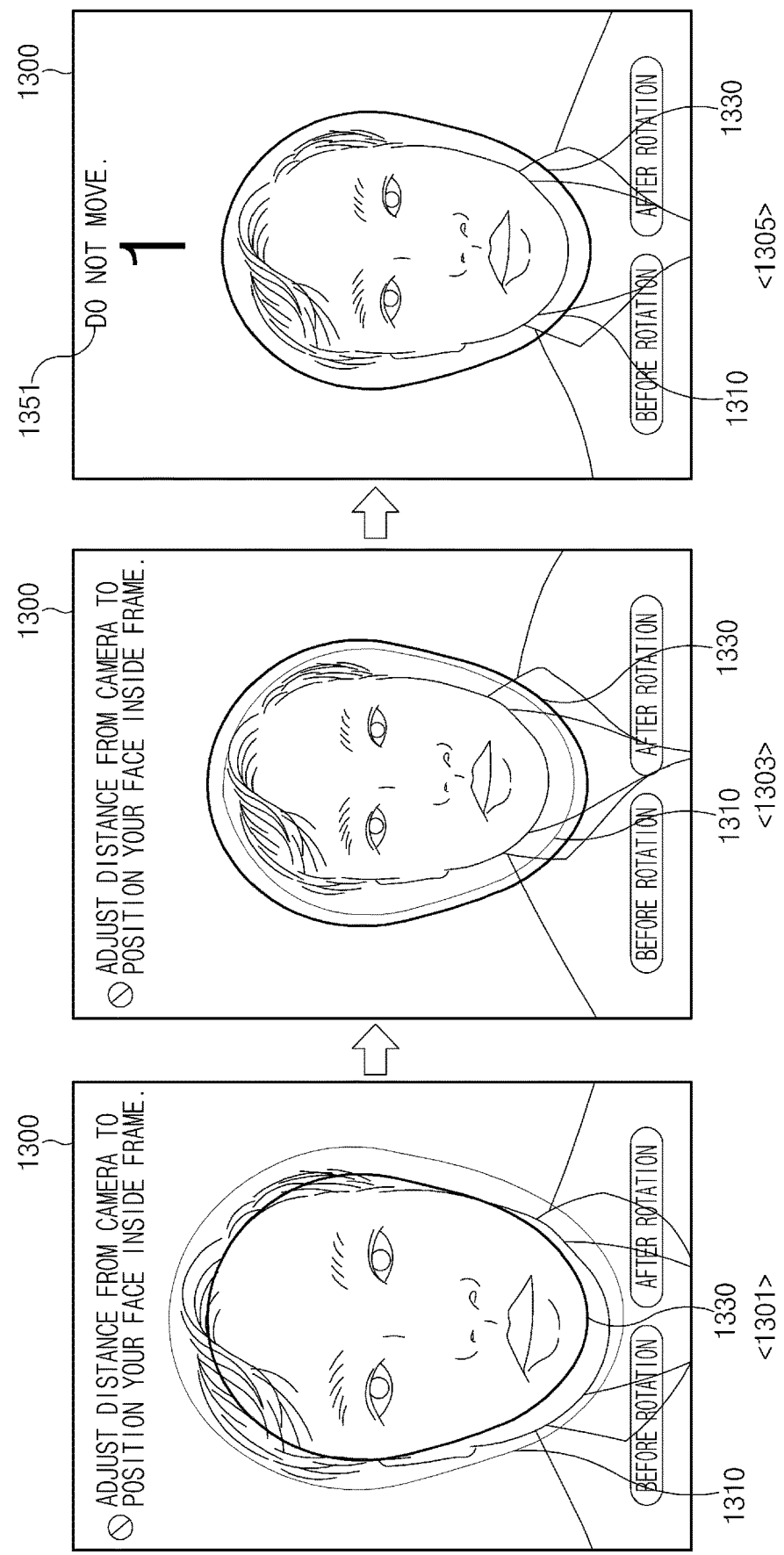
FIG. 13 illustrates an object providing a guide for maintaining an alignment state of a skin region to be captured, according to an embodiment.

FIG. 13 illustrates an object providing a guide for maintaining an alignment state of a skin region to be captured, according to an embodiment.

Referring to FIG. 13, a processor 130 of an electronic device 100 may display, on a preview image 1300, a guide object 1330 for guiding the alignment state of a subject captured through a camera 110. For example, the processor may display, on the preview image 1300, the guide object 1330 for guiding the movement of the subject, such that the subject, i.e., the user's face, is positioned at a specified region of the imaging region by the camera.

As illustrated in a first state 1301, the processor may not perform a capturing function when an object 1310 corresponding to a face is not aligned with the guide object 1330, even though the external light source is positioned in a specified direction (e.g., the front-central direction) with respect to the face.

As illustrated in a second state 1303, when the user moves the face or moves the camera, the processor may determine the size or the position of the object 1310 corresponding to the face and may change the size or the position of the object 1310 corresponding to the face based on the determination.

As illustrated in a third state 1305, when the user aligns the object 1310 corresponding to the face with the guide object 1330 by moving his/her face or the camera, the processor may perform the capturing function. For example, the processor may perform the capturing function based on the input (e.g., an input of pressing the shutter) of the user or a setting value (e.g., a setting value for auto shooting). In addition, the processor may display, on the preview image 1300, an object 1351 for directing the user not to move.

Figure 14:
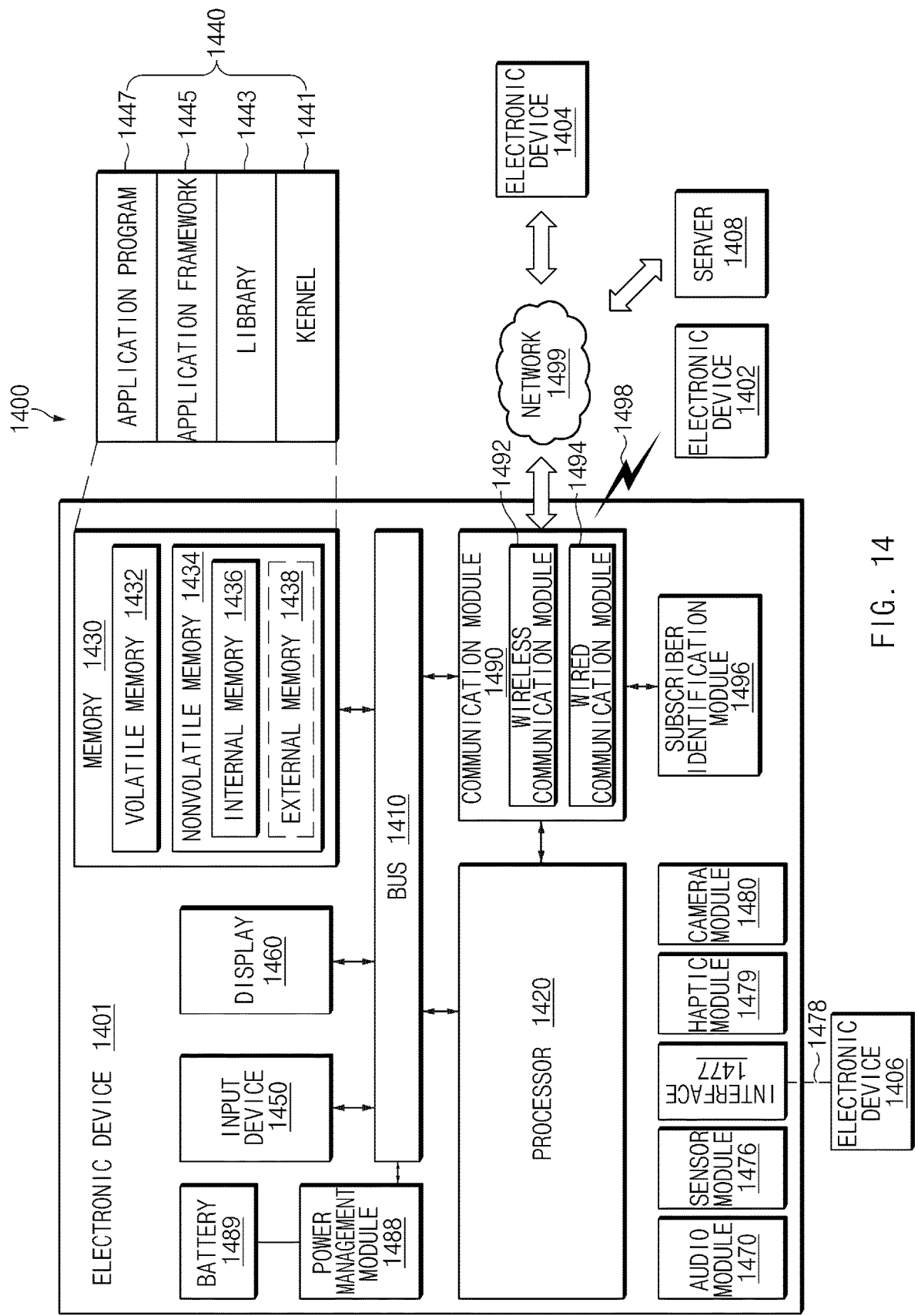
FIG. 14 illustrates an electronic device in a network environment, according to an embodiment.

FIG. 14 illustrates an electronic device in a network environment, according to an embodiment.

Referring to FIG. 14, the electronic device 1401 may include various forms of devices. For example, the electronic device 1401 may include a portable communication device (e.g., a smartphone), a computer device (e.g., a personal digital assistant (PDA), a tablet personal computer (PC), a laptop PC, a desktop PC, a workstation, or a server), a portable multimedia device (e.g., an electronic book reader or a Motion Picture Experts Group (MPEG-1 or MPEG-2) Audio Layer 3 (MP3) player), a portable medical device (e.g., a heartbeat measuring device, a blood glucose monitoring device, a blood pressure measuring device, and a body temperature measuring device), a camera, or a wearable device. The wearable device may include an accessory type device (e.g., a watch, a ring, a bracelet, an anklet, a necklace, glasses, a contact lens, or a head-mounted-device (HMD)), a fabric or garment-integrated type device (e.g., an electronic apparel), a body-attached type device (e.g., a skin pad or tattoos), or a bio-implantable type device (e.g., an implantable circuit).

The electronic device 1401 may include a television (TV), a digital versatile disk (DVD) player, an audio device, an audio accessory device (e.g., a speaker, headphones, or a headset), a refrigerator, an air conditioner, a cleaner, an oven, a microwave oven, a washing machine, an air cleaner, a set-top box, a home automation control panel, a security control panel, a game console, an electronic dictionary, an electronic key, a camcorder, or an electronic picture frame.

The electronic device 1401 may include a navigation device, a satellite navigation system (e.g., a Global Navigation Satellite System (GNSS)), an event data recorder (EDR) (e.g., a black box for a car, a ship, or a plane), a vehicle infotainment device (e.g., a heads-up display for a vehicle), an industrial or a home robot, a drone, an automatic teller machine (ATM), a point of sales (POS) device, a measuring instrument (e.g., a water meter, an electricity meter, or a gas meter), or an Internet of things (IoT) device (e.g., a light bulb, a sprinkler device, a fire alarm, a thermostat, or a street lamp).

The electronic device 1401, however, is not limited to the above-described devices, and may provide functions of a plurality of devices, like smartphones, which have measurement functions of personal biometric information (e.g., a heart rate or a blood glucose level).

Herein, the term "user" may refer to a person who uses the 1401 electronic device or may refer to a device (e.g., an artificial intelligence electronic device) that uses the electronic device 1401.

In the network environment 1400, the electronic device 1401 may communicate with an electronic device 1402 through local wireless communication 1498 or may communication with an electronic device 1404 and/or a server 1408 through a network 1499. The electronic device 1401 may communicate with the electronic device 1404 through the server 1408.

The electronic device 1401 includes a bus 1410, a processor 1420, a memory 1430, an input device 1450 (e.g., a micro-phone or a mouse), a display device 1460, an audio module 1470, a sensor module 1476, an interface 1477, a haptic module 1479, a camera module 1480, a power management module 1488, a battery 1489, a communication module 1490, and a subscriber identification module 1496. The electronic device 1401 may omit at least one (e.g., the display device 1460 or the camera module 1480) of the above-described elements or may further include other element(s).

The bus 1410 may interconnect the above-described elements 1420 to 1490 and may include a circuit for conveying signals (e.g., a control message or data) between the above-described elements.

The processor 1420 may include one or more of a CPU, an AP, a graphic processing unit (GPU), an image signal processor (ISP) of a camera or a CP. The processor 1420 may be implemented with a system on chip (SoC) or a system in package (SiP). For example, the processor 1420 may drive an OS or an application to control at least one of another element (e.g., hardware or software element) connected to the processor 1420 and may process and compute various data. The processor 1420 may load a command or data, which is received from at least one of other elements (e.g., the communication module 1490), into a volatile memory 1432 to process the command or data and may store the result data into a nonvolatile memory 1434.

The memory 1430 includes the volatile memory 1432 and the nonvolatile memory 1434. The volatile memory 1432 may include a random access memory (RAM) (e.g., a dynamic RAM (DRAM), a static RAM (SRAM), or a synchronous DRAM (SDRAM)). The nonvolatile memory 1434 may include a programmable read-only memory (PROM), an one time PROM (OTPROM), an erasable PROM (EPROM), an electrically EPROM (EEPROM), a mask ROM, a flash ROM, a flash memory, a hard disk drive (HDD), or a solid-state drive (SSD). In addition, the nonvolatile memory 1434 may be configured in the form of an internal memory 1436 or the form of an external memory 1438, which is available through connection, according to the connection with the electronic device 1401.

The external memory 1438 may further include a flash drive, such as a compact flash (CF), a secure digital (SD), a micro secure digital (Micro-SD), a mini secure digital (Mini-SD), an extreme digital (xD), a multimedia card (MMC), or a memory stick. The external memory 1438 may be operatively or physically connected with the electronic device 1401 in a wired manner (e.g., a cable or a universal serial bus (USB)) or a wireless (e.g., Bluetooth) manner.

The memory 1430 may store at least one different software element, such as an instruction or data associated with the program 1440, of the electronic device 1401. The program 1440 includes a kernel 1441, a library 1443, an application framework 1445 and an application program (application) 1447.

The input device 1450 may include a microphone, a mouse, or a keyboard. The keyboard may include a keyboard physically connected or a virtual keyboard displayed through the display 1460.

The display 1460 may include a display, a hologram device, or a projector, and a control circuit to control a relevant device. The screen may include an LCD, an LED display, an OLED display, a MEMS display, or an electronic paper display. The display 1460 may be flexibly, transparently, or wearably implemented. The display 1460 may include a touch circuitry, which is able to detect a user's input such as a gesture input, a proximity input, or a hovering input or a pressure sensor (or a force sensor) that is able to measure the intensity of the pressure by the touch. The touch circuit or the pressure sensor may be implemented integrally with the display or may be implemented with at least one sensor separately from the display. The hologram device may show a stereoscopic image in a space using interference of light. The projector may project light onto a screen to display an image. The screen may be located inside or outside the electronic device 1401.

The audio module 1470 may convert from a sound into an electrical signal or from an electrical signal into the sound. The audio module 1470 may acquire sound through the input device 1450 (e.g., a microphone) or may output sound through an output device (e.g., a speaker or a receiver) included in the electronic device 1401, an external electronic device (e.g., the electronic device 1402 (e.g., a wireless speaker or a wireless headphone)) or an electronic device 1406 (e.g., a wired speaker or a wired headphone) connected with the electronic device 1401.

The sensor module 1476 may measure or detect an internal operating state (e.g., power or temperature) of the electronic device 1401 or an external environment state (e.g., an altitude, a humidity, or brightness) to generate an electrical signal or a data value corresponding to the information of the measured state or the detected state. The sensor module 1476 may include at least one of a gesture sensor, a gyro sensor, a barometric pressure sensor, a magnetic sensor, an acceleration sensor, a grip sensor, a proximity sensor, a color sensor (e.g., a red, green, blue (RGB) sensor), an infrared sensor, a biometric sensor (e.g., an iris sensor, a fingerprint senor, a heartbeat rate monitoring (HRM) sensor, an e-nose sensor, an electromyography (EMG) sensor, an electroencephalogram (EEG) sensor, an electrocardiogram (ECG) sensor), a temperature sensor, a humidity sensor, an illuminance sensor, or an UV sensor. The sensor module 1476 may further include a control circuit for controlling at least one or more sensors included therein.

The sensor module 1476 may be controlled by using the processor 1420 or a processor (e.g., a sensor hub) separate from the processor 1420. When the separate processor (e.g., a sensor hub) is used, while the processor 1420 is in a sleep state, the separate processor may operate without wakening the processor 1420 to control at least a portion of the operation or the state of the sensor module 1476.

The interface 1477 may include a high definition multimedia interface (HDMI), a universal serial bus (USB), an optical interface, a recommended standard 232 (RS-232), a D-subminiature (D-sub), a mobile high-definition link (MHL) interface, a SD card/MMC(multi-media card) interface, or an audio interface.

A connector 1478 may physically connect the electronic device 1401 and the electronic device 1406. The connector 1478 may include an USB connector, an SD card/MMC connector, or an audio connector (e.g., a headphone connector).

The haptic module 1479 may convert an electrical signal into mechanical stimulation (e.g., vibration or motion) or into electrical stimulation. For example, the haptic module 1479 may apply tactile or kinesthetic stimulation to a user. The haptic module 1479 may include a motor, a piezoelectric element, or an electric stimulator.

The camera module 1480 may capture a still image and/or a moving picture. The camera module 1480 may include at least one lens (e.g., a wide-angle lens and a telephoto lens, or a front lens and a rear lens), an image sensor, an image signal processor, or a flash (e.g., a light emitting diode or a xenon lamp).

The power management module 1488, which is to manage the power of the electronic device 1401, may constitute at least a portion of a power management integrated circuit (PMIC).

The battery 1489 may include a primary cell, a secondary cell, or a fuel cell, and may be recharged by an external power source to supply power at least one element of the electronic device 1401.

The communication module 1490 may establish a communication channel between the electronic device 1401 and an external device (e.g., the first external electronic device 1402, the second external electronic device 1404, or the server 1408). The communication module 1490 may support wired communication or wireless communication through the established communication channel. The communication module 1490 includes a wireless communication module 1492 and a wired communication module 1494. The communication module 1490 may communicate with the external device through a first network 1498 (e.g. a wireless local area network such as Bluetooth or Infrared Data Association (IrDA)) or a second network 1499 (e.g., a wireless wide area network such as a cellular network) through a relevant module among the wireless communication module 1492 or the wired communication module 1494.

The wireless communication module 1492 may support cellular communication, local wireless communication, or global navigation satellite system (GNSS) communication. The cellular communication may include long-term evolution (LTE), LTE Advance (LTE-A), code division multiple access (CDMA), wideband CDMA (WCDMA), universal mobile telecommunications system (UMTS), wireless broadband (WiBro), or global system for mobile communications (GSM). The local wireless communication may include Wi-Fi, WiFi Direct, light fidelity (Li-Fi), Bluetooth, Bluetooth low energy (BLE), Zigbee, near field communication (NFC), magnetic secure transmission (MST), radio frequency (RF), or a body area network (BAN). The GNSS may include at least one of a global positioning system (GPS), a global navigation satellite system (Glonass), Beidou Navigation Satellite System (Beidou), the European global satellite-based navigation system (Galileo), etc. In the present disclosure, "GPS" and "GNSS" may be interchangeably used.

When the wireless communication module 1492 supports cellar communication, the wireless communication module 1492 may identify or authenticate the electronic device 1401 within a communication network using the subscriber identification module (SIM) 1496 (e.g., a SIM card).

The wireless communication module 1492 may include a CP separate from the processor 1420 (e.g., an AP). In this case, the CP may perform at least a portion of functions associated with at least one of elements 1410 to 1496 of the electronic device 1401 instead of the processor 1420, e.g., when the processor 1420 is in an inactive (sleep) state, and together with the processor 1420, e.g., when the processor 1420 is in an active state. The wireless communication module 1492 may include a plurality of communication modules, each supporting a relevant communication scheme among cellular communication, local wireless communication, or a GNSS communication.

The wired communication module 1494 may include a local area network (LAN) service, a power line communication, or a plain old telephone service (POTS).

For example, the first network 1498 may employ Wi-Fi direct or Bluetooth for transmitting or receiving commands or data through wireless direct connection between the electronic device 1401 and the first external electronic device 1402. The second network 1499 may include a telecommunication network (e.g., a computer network, such as a LAN or a WAN, the Internet, or a telephone network) for transmitting or receiving commands or data between the electronic device 1401 and the second electronic device 1404.

The commands or the data may be transmitted or received between the electronic device 1401 and the second external electronic device 1404 through the server 1408 connected with the second network 1499. Each of the first and second external electronic devices 1402 and 1404 may be same or different type of a device as that of the electronic device 1401.

All or a part of operations that the electronic device 1401 will perform may be executed by another or a plurality of electronic devices (e.g., the electronic devices 1402 and 1404 or the server 1408). When the electronic device 1401 executes a function or service automatically or in response to a request, instead of performing the function or the service internally, the electronic device 1401 may alternatively or additionally transmit requests for at least a part of a function associated with the electronic device 1401 to the electronic device 1402 or 1404 or the server 1408. The electronic device 1402 or 1404 or the server 1408 may execute the requested function or additional function and may transmit the execution result to the electronic device 1401. The electronic device 1401 may provide the requested function or service using the received result or may additionally process the received result to provide the requested function or service. To this end, cloud computing, distributed computing, or client-server computing may be used.

According to various embodiments, at least a part of an apparatus (e.g., modules or functions thereof) or a method (e.g., operations) may be implemented by instructions stored in a computer-readable storage media (e.g., the memory 1430) in the form of a program module. The instructions, when executed by a processor (e.g., a processor 1420), may cause the processor to perform a function corresponding to the instruction. The computer-readable recording medium may include a hard disk, a floppy disk, a magnetic media (e.g., a magnetic tape), an optical media (e.g., a compact disc read only memory (CD-ROM) and a DVD, a magneto-optical media (e.g., a floptical disk)), an embedded memory, etc. The one or more instructions may contain a code made by a compiler or a code executable by an interpreter.

According to various embodiments, the computer-readable storage (or recording) medium may have a program for executing a method comprising obtaining an image for one or more external objects through a camera, identifying an interest object, which corresponds to a face, of the one or more external objects included in the image and determining, with respect to the interest object, a first region and a second region associated with recognizing the face, determining a first brightness value for the first region and a second brightness value for the second region, determining property information of an external light source for the interest object, at least based on the first brightness value and the second brightness value, and providing, through the display, guide information corresponding to the property information in association with the interest object.

The method may further include obtaining another image for the interest object, when a difference value between the first brightness value and the second brightness value satisfies a specified condition.

The method may further include providing, through the display, a first indicator representing a reference for a size of the interest object and a second indicator varied depending on a size of the interest object, in association with the obtaining of the another image, before obtaining the another image.

Each element (e.g., a module or a program module) according to various embodiments may be composed of single entity or a plurality of entities, a part of the above-described sub-elements may be omitted or may further include other sub-elements.

Alternatively or additionally, after being integrated in one entity, some elements (e.g., a module or a program module) may identically or similarly perform the function executed by each corresponding element before integration. Operations executed by modules, program modules, or other elements may be executed by a successive method, a parallel method, a repeated method, or a heuristic method, or at least one part of operations may be executed in different sequences or omitted. Alternatively, other operations may be added.

As described above, according to above-described embodiments in the present disclosure, a position of an external light source is guided, thereby supporting image capturing while minimizing an influence of a shadow therein.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic device, comprising:
   a camera;
   a display; and
   a processor configured to:
      obtain a first image using the camera;
      identify a face included in the first image;
      determine a first brightness value for a first region of the identified face and a second brightness value for a second region of the identified face;
      determine property information of an external light source for the identified face, based on the first brightness value and the second brightness value;
      provide, through the display, guide information corresponding to the property information of the external light source for the identified face;
      obtain a second image for the identified face in response to a difference value between the first brightness value and the second brightness value satisfying a specified condition; and
      provide, before obtaining the second image; an indicator that varies based on a size of the identified face.

2. The electronic device of claim 1, wherein the processor is further configured to provide, through the display, another indicator representing a reference for a size of the identified face.

3. The electronic device of claim 2, wherein the processor is further configured to obtain the second image, based further on a determination that the first indicator is substantially equal to the second indicator in size.

4. The electronic device of claim 1, wherein the processor is further configured to include position information of the external light source in the guide information.

5. The electronic device of claim 4, wherein the processor is further configured to include information on guiding a capturing direction for positioning the external light source in a specified direction with respect to the identified face in the guide information.

6. The electronic device of claim 1, further comprising a memory,
   wherein the processor is further configured to:
      transform data, which corresponds to the image, to be in a specified image format, and
      store, in the memory, the transformed data.

7. The electronic device of claim 6, wherein the specified image format includes brightness information corresponding to the image.

8. The electronic device of claim 7, wherein the processor is further configured to determine the first brightness value and the second brightness value, based on the brightness information.

9. An electronic device, comprising:
   a camera;

a display; and a processor configured to:
- obtain an image captured through the camera;
- determine a face in the image;
- determine a region in the determined face having a longest length protruding to an outside as a first region and calculate a first brightness value corresponding to the first region;
- determine a second region in the determined face and calculate a second brightness value corresponding to the second region;
- determine a position of an external light source based on a difference value between the first brightness value and the second brightness value; and
- display, on the display, guide information corresponding to the determined position in association with the determined face.

10. The electronic device of claim 9, further comprising:
a memory,
wherein the processor is further configured to:
- transform data corresponding to the image to be in a specified image format, and store, in the memory, the transformed data.

11. The electronic device of claim 10, wherein the specified image for includes brightness information corresponding to the image.

12. The electronic device of claim 11, wherein the processor is further configured to calculate the first brightness value and the second brightness value, based on the brightness information.

13. The electronic device of claim 9, wherein the processor is further configured to:
- determine a first specified region inside the determined face as the first region; and
- determine a second specified region, which is symmetrical to the first specified region, as the second region.

14. The electronic device of claim 9, wherein the processor is further configured to:
- determine, as the second region, a region, which has a shortest length protruding to the outside, in the determined face.

15. The electronic device of claim 9, wherein the processor is further configured to include, in the guide information, information on guiding a capturing direction for positioning the external light source in a specified direction with respect to the determined face.

16. The electronic device of claim 9, wherein the processor is further configured to display, on the display, additional guide information associated with the determined face being aligned with a specified region.

17. A non-transitory computer-readable recording medium having stored thereon, a program for executing a method comprising:
- obtaining a first image through a camera;
- identifying a face included in the first image;
- determining a first brightness value for a first region of the identified face and a second brightness value for a second region of the identified face;
- determining property information of an external light source for the identified face, based on the first brightness value and the second brightness value;
- providing, through a display, guide information corresponding to the property information in association with the identified face; and
- obtaining a second image for the identified face in response to a difference value between the first brightness value and the second brightness value satisfying a specified condition,
- wherein a second indicator is provided through the display before obtaining the second image, and the second indicator varies depending on a size of the identified face.

18. The non-transitory computer-readable recording medium of claim 17, wherein the method further comprises providing, through the display, a first indicator representing a reference for a size of the identified face.

* * * * *